(12) United States Patent
Dottorini et al.

(10) Patent No.: US 12,419,308 B2
(45) Date of Patent: Sep. 23, 2025

(54) PHENYLPYRAZOLE INSECTICIDE COMPOUNDS AND COMPOSITIONS

(71) Applicant: Molecular Horizon SRL, Bettona (IT)

(72) Inventors: Francesco Dottorini, Perugia (IT); Aurora Valeri, Siena (IT); Alessandra Di Veroli, Perugia (IT)

(73) Assignee: Molecular Horizon SRL, Bettona (IT)

( * ) Notice: Subject to any disclaimer, the term of this patent is extended or adjusted under 35 U.S.C. 154(b) by 0 days.

(21) Appl. No.: 18/959,040

(22) Filed: Nov. 25, 2024

(65) Prior Publication Data
US 2025/0089719 A1 Mar. 20, 2025

Related U.S. Application Data

(63) Continuation of application No. PCT/EP2024/062844, filed on May 8, 2024.

(30) Foreign Application Priority Data

May 9, 2023 (EP) .................................... 23425020

(51) Int. Cl.
| | | |
|---|---|---|
| C07D 471/04 | (2006.01) |
| A01N 43/90 | (2006.01) |
| A01P 7/02 | (2006.01) |
| A61K 9/00 | (2006.01) |
| A61K 31/437 | (2006.01) |
| A61P 33/14 | (2006.01) |

(52) U.S. Cl.
CPC ............... *A01N 43/90* (2013.01); *A01P 7/02* (2021.08); *A61K 9/0017* (2013.01); *A61K 31/437* (2013.01); *A61P 33/14* (2018.01); *C07D 471/04* (2013.01)

(58) Field of Classification Search
CPC ...................................................... A01N 43/90
USPC ........................................................ 514/303
See application file for complete search history.

(56) References Cited

U.S. PATENT DOCUMENTS

| | | | | |
|---|---|---|---|---|
| 9,605,005 B2 * | 3/2017 | Blaquiere | ............... | A61P 37/02 |
| 2010/0331297 A1 * | 12/2010 | Bulawa | ............... | A61P 25/00 |
| | | | | 435/375 |

FOREIGN PATENT DOCUMENTS

| | | |
|---|---|---|
| CN | 109134375 | 1/2019 |
| CN | 115304607 | 11/2022 |
| WO | 2004/092140 | 10/2004 |
| WO | 2015/025025 | 2/2015 |

OTHER PUBLICATIONS

Markwalder et al., Journal of Medicinal Chemistry (2004), 47(24), 5894-5911.*
Swelam et al., Journal of the Serbian Chemical Society (1999), 64(11), 655-662.*
Liu et al., Arkivoc (Gainesville, FL, United States) (2008), Volume Date 2009, (2), 258-268.*
Al-Afaleq, et al., "Heterocyclic o-Aminonitriles: Preparation of Pyrazolo[3,4-d]-pyrimidines with Modification of the Substituents at the 1-Position", Molecules, Jun. 30, 2001, p. 621-638.
Fernández, et al., "Modeling of Cyclin-Dependent Kinase Inhibition by 1 H-Pyrazolo[3,4-d ]Pyrimidine Derivatives Using Artificial Neural Network Ensembles", Journal of Chemical Information and Modeling, vol. {0} 45, No. {0} 6, Nov. 1, 2005, p. 1884-1895.
Guo et al., "Design, synthesis, antibacterial and insecticidal activities of novel N-phenylpyrazole fraxinellone hybrid compounds" RSC Advances 2017, 7, 11796-11802.
Leemans, et al., "Pesticides With Potential Thyroid Hormone-Disrupting Effects: A Review of Recent Data" Front. Endocrinol., 2019, 10:743.
Li et al., "Design, Synthesis, Insecticidal Evaluation and Modeling Studies on 1,4,6,7-tetrahydropyrazolo[3,4-d][1,3] oxazine Derivatives: An Application of Scaffold Hopping Strategy on Fipronil" Letters in Drug Design & Discovery, 2019, 16, 1175-1180.
Li, et al., "4-Oxo-4,5,6,7-tetrahydro-1 H-pyrazolo[3,4- d ]pyrimidine Derivatives: Design, Synthesis, Insecticidal Assay and Binding Mode Studies", CH vol. {0} 19, No. {0} 8, Aug. 1, 2022, Chemistry & Biodiversity.
Liu, et al., "Chromogenic and fluorescent chemodosimeter for fluoride ion based on novel anion-catalyzed intramolecular hydrogen transfer" New Journal of Chemistry, vol. 38, 472-476, 2007.

(Continued)

*Primary Examiner* — Niloofar Rahmani
(74) *Attorney, Agent, or Firm* — Hoxie & Associates LLC

(57) ABSTRACT

The present disclosure relates to new and improved insecticidal compounds of the phenylpyrazole class, according to the Formula I:

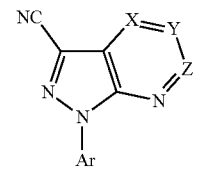

wherein X, Y, Z, and Ar are as defined herein. In particular, the disclosure provides new insecticidal compounds for use against a variety of insects (arthropods), such as, for the treatment or prevention of disease or infestation on poultry and other livestock, horses, cats, dogs, and other companion animals, fields, crops, and other insecticidal uses. In particular embodiments, the present disclosure provides the use of said compounds for the treatment, control, suppression, or eradication, of an infection or infestation of an insect (arthropod), such as an adult insect, insect egg, insect larva, insect nymph, and/or insect pupa, including, but not limited to, the poultry mite, *Dermanyssus gallinae*.

20 Claims, No Drawings

(56) References Cited

OTHER PUBLICATIONS

Liu, et al., "Crystal structure and mechanistic investigation of the reaction of 5-amino-1-(2,6-dichloro-4-(trifluoromethyl) phenyl)-1H-pyrazole-3-carbonitrile with unsaturated carbonyl compounds", NL vol. {0} 39, No. {0} 5, Aug. 4, 2012.

Liu, et al., "One-step, facile synthesis of pyrazolopyridines and tetrahydropyrazolopyridines through disproportionation of initially formed pyrazolo Hantzsch dihydropyridine", Arkivoc, vol. {0} 2009, No. {0} 2, Apr. 27, 2009, p. 258-268.

Swelam, et al., "Synthesis of some pyrazolo[3,4-d]pyrimidines and their fused triazole and tetrazole derivatives" J. Serb. Chem. Soc. 64(11), 655-662, 1999.

\* cited by examiner

PHENYLPYRAZOLE INSECTICIDE COMPOUNDS AND COMPOSITIONS

CROSS REFERENCE TO RELATED APPLICATION

The instant application is U.S. national application filed under 35 U.S.C. § 111 (a) which is a continuation of international PCT application No. PCT/EP2024/062844, filed on May 8, 2024, which claims priority to European Application No. 23425020.7, filed on May 9, 2023, the contents of which are hereby incorporated by reference in its entirety.

FIELD OF THE INVENTION

This present disclosure relates to new and improved insecticidal compounds of the phenylpyrazole class. In particular, the disclosure provides new insecticidal compounds for use against a variety of insects (arthropods), such as, for the treatment or prevention of disease or infestation on poultry and other livestock, horses, cats, dogs, and other companion animals, fields, crops, and other insecticidal uses.

BACKGROUND OF THE INVENTION

Insecticides are agents of chemical or biological origin which are used to control the growth of insect (arthropods) pests, primarily by either killing then or by inhibiting a critical step in the insect's lifecycle (e.g., a stage such as the egg, larva, nymph, pupa, and/or adult). Insecticides may either exert their effect acutely, such as after a single exposure, or after chronic exposure. There are a variety of ways in which insecticides can be disseminated, depending on the nature of the pest. Of the more than 5-10 million arthropod species known, including more than 1 million species of true insects known, many thousands are considered pests or parasites. Some are responsible for the destruction of crops, and this constitutes the bulk of commercial insecticide usage. Other insects cause disease in animals, including humans, companion animals (dogs, cats, horses, etc.), and livestock (e.g., poultry, cattle, pigs, sheep, goats).

Insecticides have a variety of modes of action, although primarily they affect the insect nervous system, usually as potent neurotoxins. For example, organochlorine insecticides (e.g., DDT) and pyrethroid insecticides promote sodium channel opening, organophosphate and carbamate insecticides inhibit the acetylcholinesterase enzyme, neonicotinoid insecticides inhibit the nicotinic acetylcholine receptor, and phenylpyrazole insecticides inhibit the GABA-gated chloride channel.

The phenylpyrazole class of insecticides are broad-spectrum insecticides and are among the most commonly used insecticides. Phenylpyrazole insecticides act on the GABA (gamma-aminobutyric acid) receptor on the neurons of insects, blocking chloride ion conduction. Because chloride ion influx into neurons is an inhibitory action, disruption of GABA receptor opening results in a hyperexcited state in the neurons. Fipronil was the first phenylpyrazole insecticide, introduced in 1993 These agents were developed specifically to address the widespread resistance of insects to older classes of insecticides. In particular, fipronil has been used against insects which have become tolerant of pyrethroid, organophosphate, and carbamate insecticides, including cockroaches, beetles, ants, fleas, termites, ticks, weevils, mole crickets, flies, mosquitos, and moths. Other phenylpyrazole class insecticides include acetoprole, ethiprole, flufiprole, pyraclofos, pyrafluprole, pyriprole, pyrolan, and vanilliprole. While these compounds share an N-phenylpyrazole ring, they are otherwise quite structurally diverse:

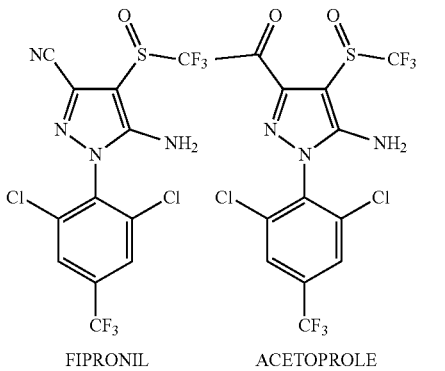

FIPRONIL ACETOPROLE

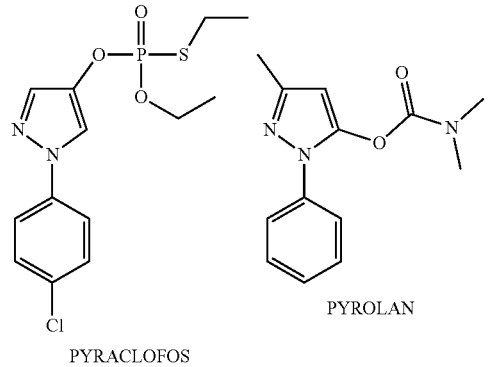

PYRACLOFOS PYROLAN

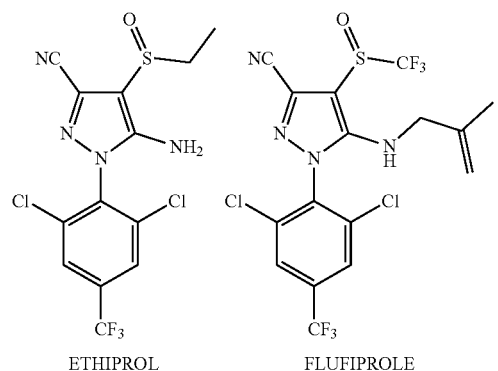

ETHIPROL FLUFIPROLE

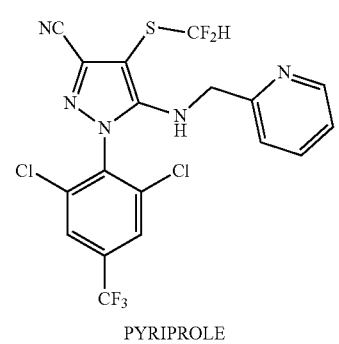

PYRIPROLE

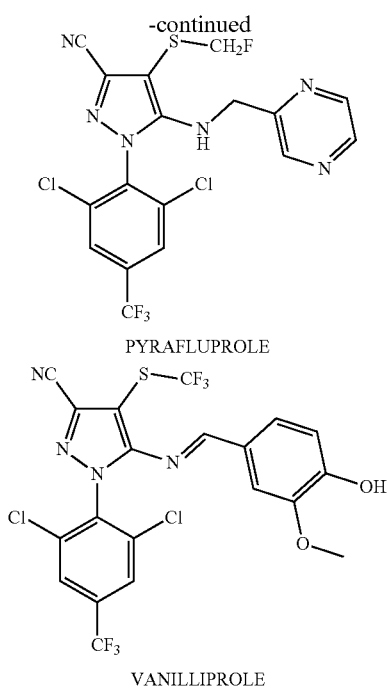

PYRAFLUPROLE

VANILLIPROLE

After they were introduced, the phenylpyrazole insecticides played a crucial role in controlling pests in crop, livestock, and companion animal uses. However, their extensive use has also already led to the development of resistance. In addition, while phenylpyrazoles are generally relatively safe to mammals (due to structural differences between insect and mammalian GABA receptors), fipronil has recently been banned in many countries for certain uses due to high toxicity to non-target beneficial organisms, including fish, aquatic invertebrates, and bees. See, e.g., Li et al, *Letters in Drug Design & Discovery,* 2019, 16, 1175-1180; Guo et al., *RSC Advances* 2017, 7, 11796-11802; Leemans et al, *Front. Endocrinol.,* 2019, 10:743. Leemans et al characterize fipronil as a widespread environmental contaminant, being found in soil, water, outdoor dust, and some food products. Fipronil is thought to be cytotoxic to epithelial cells, including intestinal epithelium, if ingested in sufficient quantities, fipronil can cause nausea, vomiting, abdominal pain, seizures, and toxic effects on the kidneys, liver and thyroid glands.

Fipronil was linked to mass bee die-offs in France in the 1990's and 2000's, resulting in it being banned as a crop insecticide by the European Commission in 2014, as well as banned for use on animals intended for human consumption. While environmental degradation of fipronil is slow, metabolic degradation in animals is rapid. Contributing to the risk of oral toxicity, the primary metabolites of fipronil—the sulfone, the sulfide, and the desulfinylated derivative, are considerably more toxic, persistent, bioaccumulative, and less selective than the parent compound. See Leemans et al

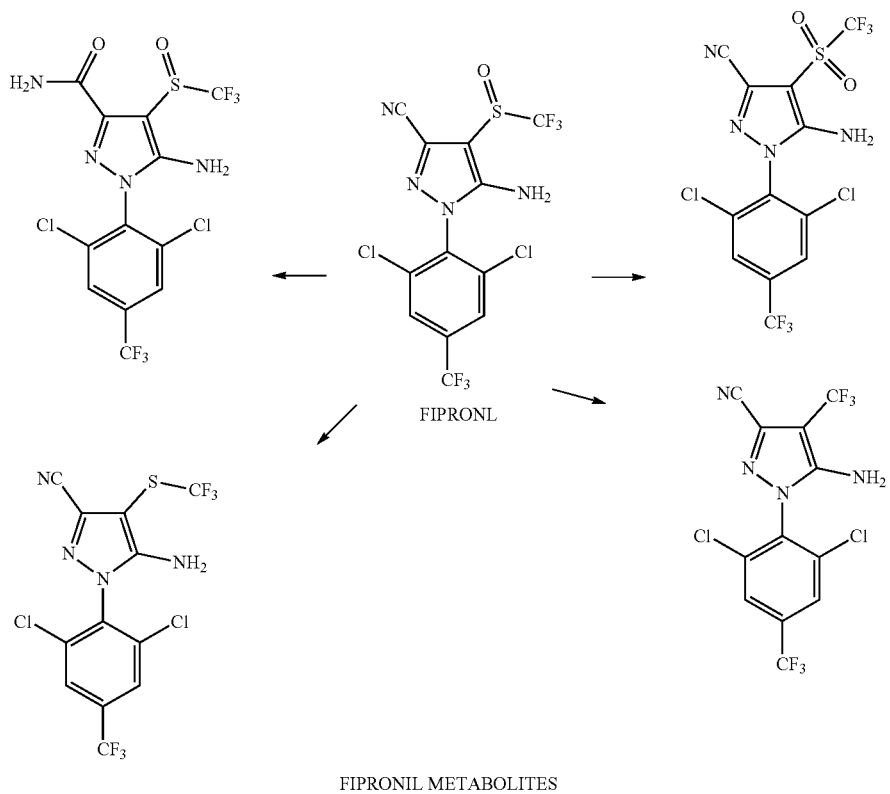 [SMILES: NC(=O)c1nn(-c2c(Cl)cc(C(F)(F)F)cc2Cl)c(N)c1S(=O)C(F)(F)F ; N#Cc1nn(-c2c(Cl)cc(C(F)(F)F)cc2Cl)c(N)c1S(=O)C(F)(F)F ; N#Cc1nn(-c2c(Cl)cc(C(F)(F)F)cc2Cl)c(N)c1S(=O)(=O)C(F)(F)F ; N#Cc1nn(-c2c(Cl)cc(C(F)(F)F)cc2Cl)c(N)c1SC(F)(F)F ; N#Cc1nn(-c2c(Cl)cc(C(F)(F)F)cc2Cl)c(N)c1C(F)(F)F]

FIPRONIL METABOLITES

Fipronil has long been used to treat ectoparasites infecting poultry, such as fleas, lice, and ticks (particularly the poultry mite or red mite, *Dermanyssus gallinae*). However, in the EU, fipronil was banned for use in poultry for human consumption from 2013 to 2019. In 2017, a serious scandal rocked the continent when fipronil was detected in eggs on the European market. This was the result of pesticide vendors illegally selling fipronil-containing products to unknowing farmers. As a result, millions of eggs were pulled from the market, millions of chickens were slaughtered, and the proprietors of the pesticide vendors faced jail time. Nevertheless, in 2018, the judicial court of the EU reversed some aspects of the fipronil ban, on the ground of insufficient evidence, but there remain calls to completely ban fipronil from the EU marketplace.

Thus, there has been work done to try to replace fipronil. Li et al., observed that molecular modeling predicted the existence of an intramolecular hydrogen bond between the amino group and the sulfoxide oxygen in fipronil, and they therefore devised a series of 1,4,6,7-tetrahydropyrazolo[3,4-d]oxazine derivatives:

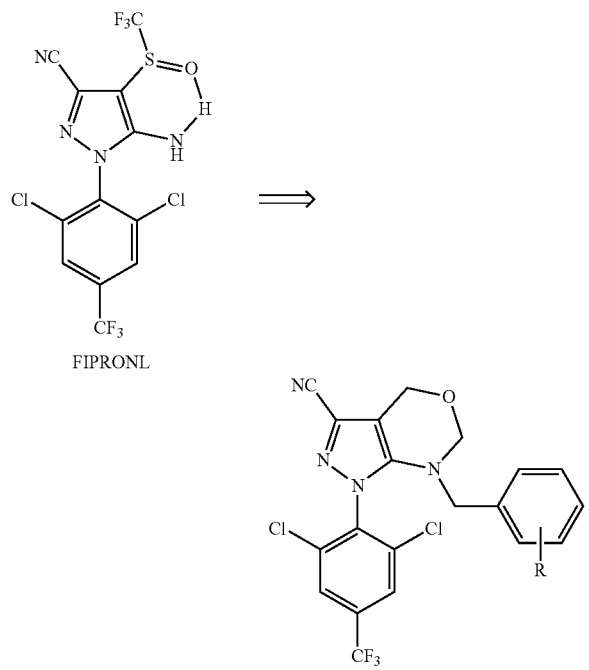

Li et al, prepared and tested 25 compounds, but only four of the compounds had measurable insecticidal activity, peaking at only about 60% of fipronil's activity against *Plutella xylostella*, none of which had insecticidal activity comparable to fipronil. The authors speculated that the disappointing result could have been due to differences in physicochemical properties, There exists a continuing need for effective methods for controlling pests in crop, livestock, and companion animal uses, without the risk of accumulation of the agent in the animal, such as in food products derived from the animal, and preferably avoiding the formation of potentially dangerous metabolites.

SUMMARY OF THE INVENTION

The present disclosure provides new V-phenyl-1H-pyrazolo[3,4-b]pyridine-3-carbonitriles, which are effective as insecticidal agents for crop, livestock, human, companion animal, and other insecticidal uses.

In a first aspect, the present disclosure provides a Compound of Formula I (Compound 1) having the following general structure:

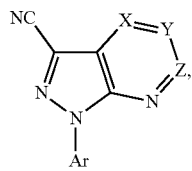

wherein:

X is —N— or —$CR^1$—;

Y is —N— or —$CR^2$—;

Z is —$CR^3$—;

$R^1$, $R^2$, and $R^3$ are each independently selected from H, halo, cyano, nitro, hydroxy, amino, $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ cycloalkoxy, $C_{3-6}$ halocycloalkyl, NH($C_{1-6}$ alkyl), N($C_{1-6}$ alkyl)($C_{1-6}$ alkyl), and 3-6 membered heterocycloalkyl, each of which is optionally substituted;

Ar is phenyl or 5- or 6-membered heteroaryl, optionally substituted by 1-5 groups R; and each R is independently selected from halo, cyano, nitro, hydroxy, amino, $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ halocycloalkyl, NH($C_{1-6}$ alkyl), N($C_{1-6}$ alkyl)($C_{1-6}$ alkyl), and 3-6 membered heterocycloalkyl, each of which is optionally substituted;

in free or salt form.

In a second aspect, the present disclosure a pharmaceutical or insecticidal composition comprising an effective amount of a Compound of Formula I, in free or salt form, in admixture with a pharmaceutically acceptable or insecticidally acceptable diluent or carrier. In certain embodiments, the compositions as described herein may be used for, or are intended for use to treat, control, suppress, or eradicate, an infection or infestation of an insect (arthropod), such as adult insect, insect egg, insect larva, insect nymph, and/or insect pupa, for example, in an animal or human patient in need thereof or in a product or location in need thereof.

In another aspect, the present disclosure provides a method (Method 1) for the treatment, control, suppression, or eradication, of an infection or infestation of an insect (arthropod), such as an adult insect, insect egg, insect larva, insect nymph, and/or insect pupa, comprising administering or applying an effective amount of a compound of Formula T, in free or salt form, or a composition comprising a compound of Formula I, in free or salt form, as described herein, to an animal or human patient in need thereof or to a product or location in need thereof.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclosure. The publications and other materials used herein to illuminate the background of the invention, and in particular cases, to provide additional details respecting the practice, are incorporated by reference. Where applicable or not specifically disclaimed, any one of the embodiments described herein are contemplated to be able to combine with any other one or more embodiments, even though the embodiments are described under different aspects of the disclosure.

DETAILED DESCRIPTION

The following is a detailed description provided to aid those skilled in the art in practicing the invention of the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present disclosure provides new N-phenyl-1H-pyrazolo[3,4-b]pyridine-3-carbonitriles, which are effective as insecticidal agents for crop, livestock, human, companion animal, and other insecticidal uses.

In a first aspect, the present disclosure provides a Compound of Formula I (Compound 1) having the following general structure:

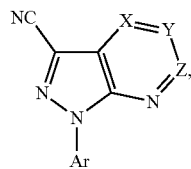

Formula I wherein:
X is —N— or —CR$^1$;
Y is —N— or —CR$^2$;
Z is —CR;
R$^1$, R$^2$, and R$^3$ are each independently selected from H, halo, cyano, nitro, hydroxy, amino, C$_{1-6}$ alkyl, C$_{3-6}$ cycloalkyl, C$_{1-6}$ haloalkyl, C$_{3-6}$ alkoxy, C$_{1-6}$ haloalkoxy, C$_{3-6}$ cycloalkoxy, C$_{3-6}$ halocycloalkyl, NH(C$_{1-6}$ alkyl), N(C$_{1-6}$ alkyl)(C$_{1-6}$ alkyl), and 3-6 membered heterocycloalkyl, each of which is optionally substituted;
Ar is phenyl or 5- or 6-membered heteroaryl, optionally substituted by 1-5 groups R; and
each R is independently selected from halo, cyano, nitro, hydroxy, amino, C$_{1-6}$ alkyl, C$_{3-6}$ cycloalkyl, C$_{1-6}$ haloalkyl, C$_{1-6}$ alkoxy, C$_{1-6}$ haloalkoxy, C$_{3-6}$ halocycloalkyl, NH(C$_{1-6}$ alkyl), N(C$_{1-6}$ alkyl)(C$_{1-6}$ alkyl), and 3-6 membered heterocycloalkyl, each of which is optionally substituted;
in free or salt form.

In further embodiments of the first aspect, the present disclosure provides:
1.1 Compound 1, wherein X is N;
1.2 Compound 1, wherein X is —CR$^1$—;
1.3 Compound 1 or 1.2, wherein R$^1$ is selected from H, halo (e.g., F, Cl), cyano, nitro, hydroxy, amino, C$_{1-6}$ alkyl (e.g., methyl, ethyl), C-A cycloalkyl (e.g., cyclopropyl), C$_{1-6}$ haloalkyl (e.g., trifluoromethyl), C$_{1-6}$ alkoxy (e.g., methoxy, ethoxy), C$_1$ haloalkoxy (e.g., trifluoromethoxy), C$_{3-6}$ cycloalkoxy (e.g., cyclopropoxy), C$_{3-6}$halocycloalkyl (e.g., 2,2-difluorocyclopropyl), NH(C$_{1-6}$alkyl) (e.g., N-methylamino), N(C$_{1-6}$ alkyl)(C$_{1-6}$ alkyl) (e.g., N,N-dimethylamino), and 3-6 membered heterocycloalkyl (e.g. aziridinyl, azetidinyl, pyrrolidinyl), each of which is optionally substituted;
1.4 Compound 1.3, wherein R$^1$ is selected from H, halo (e.g., F, Cl), cyano, nitro, hydroxy, amino, C$_{1-6}$ alkyl (e.g., methyl, ethyl), C$_{3-6}$ cycloalkyl (e.g., cyclopropyl), C$_{1-6}$haloalkyl (e.g., trifluoromethyl), C$_{1-6}$ alkoxy (e.g., methoxy, ethoxy), C$_{1-6}$ haloalkoxy (e.g., trifluoromethoxy), and C$_{3-6}$ cycloalkoxy (e.g., cyclopropoxy), each of which is optionally substituted;
1.5 Compound 1.4, wherein R$^1$ is selected from H, halo (e.g., F, Cl), cyano, nitro, C$_{1-6}$ alkyl (e.g., methyl, ethyl), C$_{3-6}$ cycloalkyl (e.g., cyclopropyl), C$_{1-6}$ haloalkyl (e.g., trifluoromethyl), C$_{1-6}$ alkoxy (e.g., methoxy, ethoxy), and C$_{1-6}$ haloalkoxy (e.g., trifluoromethoxy), each of which is optionally substituted;
1.6 Compound 1.5, wherein R$^1$ is selected from halo (e.g., F, Cl), cyano, C$_{1-3}$ alkyl (e.g., methyl, ethyl), and C$_{1-3}$ haloalkyl (e.g., trifluoromethyl), each of which is optionally substituted;
1.7 Compound 1.5, wherein R$^1$ is selected from halo (e.g., F, Cl), cyano, C$_{1-3}$ alkyl (e.g., methyl, ethyl), C$_{3-6}$ cycloalkyl (e.g., cyclopropyl), and C$_{1-3}$ haloalkyl (e.g., trifluoromethyl), each of which is optionally substituted;
1.8 Compound 1.5, wherein R$^1$ is selected from C$_{1-3}$ alkyl (e.g., methyl, ethyl), C$_{3-6}$ cycloalkyl (e.g., cyclopropyl), and C$_{1-3}$ haloalkyl (e.g., trifluoromethyl), each of which is optionally substituted;
1.9 Compound 1.5, wherein R$^1$ is C$_{1-3}$ alkyl (e.g., methyl, ethyl), optionally substituted;
1.10 Compound 1.5, wherein R$^1$ is C$_{3-6}$ cycloalkyl (e.g., cyclopropyl), optionally substituted;
1.11 Compound 1.5, wherein R$^1$ is C$_{1-3}$ haloalkyl (e.g., trifluoromethyl), optionally substituted;
1.12 Compound 1 or any of 1.2-1.11, wherein said alkyl, cycloalkyl, haloalkyl, alkoxy, haloalkoxy, cycloalkoxy, halocycloalkyl, or heterocycloalkyl of R$^1$ is unsubstituted;
1.13 Compound 1 or any of 1.2-1.11, wherein said alkyl, cycloalkyl, haloalkyl, alkoxy, haloalkoxy, cycloalkoxy, halocycloalkyl, or heterocycloalkyl of R$^1$ is substituted by one or more groups R$^a$, wherein R$^a$ is selected from halo, hydroxy, cyano, nitro, amino, C$_{1-6}$ alkyl, C$_{3-6}$ cycloalkyl, C$_{1-6}$ haloalkyl, C$_{1-6}$ alkoxy, C$_{1-6}$ haloalkoxy, C$_{3-6}$ cycloalkoxy, C$_{3-6}$ halocycloalkyl, NH(C$_{1-6}$ alkyl), N(C$_{1-6}$ alkyl)(C$_{1-6}$ alkyl), and 3-6 membered heterocycloalkyl, each of which is further optionally substituted by one or more groups R$^b$, wherein R$^b$ is selected from halo, hydroxy, cyano, nitro, hydroxy, amino, C$_{1-6}$ alkyl, C$_{3-6}$ cycloalkyl, C$_{1-6}$haloalkyl, C$_{1-6}$alkoxy, C$_{1-6}$ haloalkoxy, C$_{3-6}$ cycloalkoxy, C$_{3-6}$ halocycloalkyl, NH(C$_{1-6}$alkyl), N(C$_{1-6}$ alkyl)(C$_{1-6}$ alkyl), and 3-6 membered heterocycloalkyl;
1.14 Compound 1, or any of 1.2-1.13, wherein R$^1$ is selected from H, F, Cl, Br, I, cyano, nitro, hydroxy, amino, methyl, ethyl, propyl, isopropyl, n-butyl, isobutyl, sec-butyl, tert-butyl, cyclopropyl, cyclobutyl, fluoromethyl, difluoromethyl, trifluoromethyl, chloromethyl, dichloromethyl, trichloromethyl, methoxy, ethoxy, propoxy, isopropoxy, fluoromethoxy, difluoromethoxy, trifluoromethoxy, cyclopropoxy, cyclobutoxy, 2,2-difluorocyclopropyl, N-methylamino, N-ethylamino, N,N-dimethylamino, N,N-diethylamino, N-ethyl-N-methylamino, aziridinyl, azetidinyl, pyrrolidinyl, oxetanyl tetrahydrofuranyl, morpholino, piperidinyl, and piperazinyl;

1.15 Compound 1.14, wherein $R^1$ is selected from H, F, Cl, Br, I, cyano, nitro, hydroxy, amino, methyl, ethyl, propyl, isopropyl, cyclopropyl, cyclobutyl, fluoromethyl, difluoromethyl, trifluoromethyl, methoxy, ethoxy, fluoromethoxy, difluoromethoxy, trifluoromethoxy, cyclopropoxy, aziridinyl, azetidinyl, and oxetanyl;

1.16 Compound 1.15, wherein $R^1$ is selected from H, F, Cl, Br, I, cyano, methyl, ethyl, isopropyl, cyclopropyl, fluoromethyl, difluoromethyl, trifluoromethyl, methoxy, ethoxy, fluoromethoxy, difluoromethoxy, trifluoroethoxy, cyclopropoxy, aziridinyl, azetidinyl, and oxetanyl;

1.17 Compound 1.16, wherein $R^1$ is selected from H, F, Cl, Br, I, cyano, methyl, fluoromethyl, difluoromethyl, and trifluoromethyl;

1.18 Compound 1.17, wherein $R^1$ is selected from fluoromethyl, difluoromethyl, and trifluoromethyl;

1.19 Compound 1.18, wherein $R^1$ is trifluoromethyl;

1.20 Compound 1, or any of 1.2-1.13, wherein $R^1$ is selected from methyl, ethyl, isopropyl, $d_3$-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl;

1.21 Compound 1.20, wherein $R^1$ is selected from methyl, isopropyl, cd-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl;

1.22 Compound 1.20, wherein $R^1$ is selected from methyl, isopropyl, $d_3$-methyl, and cyclopropyl;

1.23 Compound 1.20, wherein $R^1$ is selected from fluoromethyl, difluoromethyl, trifluoromethyl, chloromethyl, dichloromenthyl, trichloromethyl, chlorofluoromethyl, chlorodifluoromethyl, bromodifluoromethyl, and 1,1-difluoroethyl;

1.24 Compound 1.20, wherein $R^1$ is difluoromethyl;

1.25 Compound 1 or any of 1.1-1.24, wherein Y is N;

1.26 Compound 1 or any of 1.1-1.24, wherein Y is —$CR^2$—;

1.27 Compound 1 or 1.26, wherein $R^2$ is selected from H, halo (e.g., F, Cl), cyano, nitro, hydroxy, amino, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), $C_{1-6}$ haloalkoxy (e.g., trifluoromethoxy), $C_{3-6}$ cycloalkoxy (e.g., cyclopropoxy), $C_{3-6}$ halocycloalkyl (e.g., 2,2-difluorocyclopropyl), NH($C_{1-6}$alkyl) (e.g., N-methylamino), N($C_{1-6}$ alkyl)($C_{1-6}$ alkyl) (e.g., N,N-dimethylamino), and 3-6 membered heterocycloalkyl (e.g., aziridinyl, azetidinyl, pyrrolidinyl), each of which is optionally substituted;

1.28 Compound 1.27, wherein $R^2$ is selected from H, halo (e.g., F, Cl), cyano, hydroxy, amino, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), $C_{1-6}$ haloalkoxy (e.g., trifluoromethoxy), and $C_{3-6}$ cycloalkoxy (e.g., cyclopropoxy), each of which is optionally substituted;

1.29 Compound 1.28, wherein $R^2$ is selected from H, halo (e.g., F, Cl), cyano, hydroxy, $C_{1-3}$ alkyl (e.g., methyl, ethyl), $C_{1-3}$ haloalkyl (e.g., trifluoromethyl), $C_{1-3}$ alkoxy (e.g., methoxy, ethoxy), and $C_{1-3}$ haloalkoxy (e.g., trifluoromethoxy), each of which is optionally substituted;

1.30 Compound 1.29, wherein R is selected from H, halo (e.g., F, Cl), cyano, $C_{1-3}$ alkyl (e.g. methyl, ethyl), and $C_{1-3}$ haloalkyl (e.g., trifluoromethyl), each of which is optionally substituted;

1.31 Compound 1.30, wherein $R^2$ is selected from H, halo (e.g., F, Cl), and cyano;

1.32 Compound 1.31, wherein $R^2$ is H;

1.33 Compound 1 or any of 1.27-1.30, wherein said alkyl, cycloalkyl, haloalkyl, alkoxy, haloalkoxy, cycloalkoxy, halocycloalkyl, or heterocycloalkyl of $R^2$ is unsubstituted;

1.34 Compound 1 or any of 1.27-1.30, wherein said alkyl, cycloalkyl, haloalkyl, alkoxy, haloalkoxy, cycloalkoxy, halocycloalkyl, or heterocycloalkyl of $R^2$ is substituted by one or more groups $R^a$, wherein $R^a$ is selected from halo, hydroxy, cyano, nitro, hydroxy, amino. $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ cycloalkoxy, $C_{3-6}$ halocycloalkyl, NH($C_{1-6}$ alkyl), N($C_{1-6}$ alkyl)($C_{1-6}$ alkyl), and 3-6 membered heterocycloalkyl, each of which is further optionally substituted by one or more groups $R^b$, wherein $R^b$ is selected from halo, hydroxy, cyano, nitro, hydroxy, amino, $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ cycloalkoxy, $C_{3-6}$ halocycloalkyl, NH($C_{1-6}$ alkyl), N($C_{1-6}$ alkyl)($C_{1-6}$ alkyl), and 3-6 membered heterocycloalkyl;

1.35 Compound 1, or any of 1.27-1.34, wherein $R^2$ is selected from H, F, Cl, Br, I, cyano, nitro, hydroxy, amino, methyl, ethyl, propyl, isopropyl, n-butyl, isobutyl, sec-butyl, tert-butyl, cyclopropyl, cyclobutyl, fluoromethyl, difluoromethyl, trifluoromethyl, chloromethyl, dichloromethyl, trichloromethyl, methoxy, ethoxy, propoxy, isopropoxy, fluoromethoxy, difluoromethoxy, trifluoromethoxy, cyclopropoxy, cyclobutoxy, 2,2-difluorocyclopropyl, N-methylamino, N-ethylamino, N,N-dimethylamino, N,N-diethylamino, N-ethyl-N-methylamino, aziridinyl, azetidinyl, pyrrolidinyl, oxetanyl, tetrahydrofuranyl, morpholino, piperidinyl, and piperazinyl;

1.36 Compound 1.35, wherein $R^2$ is selected from H, F, Cl, Br, I, cyano, hydroxy, amino, methyl, ethyl, cyclopropyl, fluoromethyl, difluoromethyl, trifluoromethyl, chloromethyl, dichloromethyl, trichloromethyl, and methoxy, 1.37 Compound 1.36, wherein $R^2$ is selected from H, F, Cl, Br, I, cyano, hydroxy, amino, methyl, fluoromethyl, difluoromethyl, and trifluoromethyl;

1.38 Compound 1.37, wherein $R^2$ is selected from H, F, Cl, Br, and cyano, optionally wherein $R^2$ is H;

1.39 Compound 1, or any of 1.1-1.38, wherein $R^1$ selected from H, halo (e.g., F, Cl), cyano, nitro, hydroxy, amino, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), $C_{1-6}$haloalkoxy (e.g., trifluoromethoxy), $C_{3-6}$ cycloalkoxy (e.g., cyclopropoxy), $C_{3-6}$ halocycloalkyl (e.g., 2,2-difluorocyclopropyl), NH($C_{1-6}$ alkyl) (e.g., N-methylamino), N($C_{1-6}$ alkyl)($C_{1-6}$ alkyl) (e.g., N,N-dimethylamino), and 3-6 membered heterocycloalkyl (e.g., aziridinyl, azetidinyl, pyrrolidinyl), each of which is optionally substituted;

1.40 Compound 1.39, wherein $R^3$ selected from H, halo (e.g., F, Cl), cyano, nitro, hydroxy, amino, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), NH($C_{1-6}$alkyl) (e.g., N-methylamino), N($C_{1-6}$ alkyl)($C_{1-6}$ alkyl) (e.g., N,N-dimethylamino), and 3-6 membered heterocycloalkyl (e.g., aziridinyl, azetidinyl, pyrrolidinyl), each of which is optionally substituted;

1.41 Compound 1.40, wherein $R^3$ selected from hydroxy, amino, $C_{1-6}$ alkyl (e.g., methyl, ethyl), NH($C_{1-6}$ alkyl) (e.g., N-methylamino), N($C_{1-6}$ alkyl)($C_{1-6}$ alkyl) (e.g., N,N-dimethylamino), and 3-6 membered heterocycloalkyl (e.g., aziridinyl, azetidinyl, pyrrolidinyl), each of which is optionally substituted;

1.42 Compound 1.41, wherein $R^3$ selected from hydroxy, amino, and NH($C_{1-6}$ alkyl) (e.g., N-methylamino), each of which is optionally substituted;

1.43 Compound 1.42, wherein $R^3$ selected from hydroxy, amino, and N-methylamino.

1.44 Compound 1.43, wherein $R^3$ is hydroxy;

1.45 Compound 1 or any of 1.39-1.42, wherein said alkyl, cycloalkyl, haloalkyl, alkoxy, haloalkoxy, cycloalkoxy, halocycloalkyl, or heterocycloalkyl of $R^3$ is unsubstituted;

1.46 Compound 1, or any of 1.1-1.42, wherein said alkyl, cycloalkyl, haloalkyl, alkoxy, haloalkoxy, cycloalkoxy, halocycloalkyl, or heterocycloalkyl of $R^3$ is substituted by one or more groups $R^a$, wherein $R^a$ is selected from halo, hydroxy, cyano, nitro, hydroxy, amino, $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ cycloalkoxy, $C_{3-6}$ halocycloalkyl, NH($C_{3-6}$ alkyl) N($C_{1-6}$ alkyl)($C_{1-6}$ alkyl), and 3-6 membered heterocycloalkyl, each of which is further optionally substituted by one or more groups $R^b$, wherein $R^b$ is selected from halo, hydroxy, cyano, nitro, hydroxy, amino, $C_{1-6}$alkyl, $C_{3-6}$ cycloalkyl, $C_{1-6}$ haloalkyl, $C_{1-6}$alkoxy, $C_{1-6}$haloalkoxy, $C_{3-6}$ cycloalkoxy, $C_{3-6}$ halocycloalkyl, NH($C_{1-6}$alkyl), N($C_{1-6}$ alkyl)($C_{1-6}$alkyl), and 3-6 membered heterocycloalkyl;

1.47 Compound 1.46, wherein $R^a$ or $R^b$ is hydroxy or amino;

1.48 Compound 1, or any of 1.1-1.42, wherein $R^3$ is selected from H, F, Cl, Br, I, cyano, nitro, hydroxy, amino, methyl, ethyl, propyl, isopropyl, n-butyl, isobutyl, sec-butyl, tert-butyl, cyclopropyl, cyclobutyl, fluoromethyl, difluoromethyl, trifluoromethyl, chloromethyl, dichloromethyl, trichloromethyl, methoxy, ethoxy, propoxy, isopropoxy, fluoromethoxy, difluoromethoxy, trifluoromethoxy, cyclopropoxy, cyclobutoxy, 2,2-difluorocyclopropyl, N-methylamino, N-ethylamino, N,N-dimethylamino, N,N-diethylamino, N-ethyl-N-methylamino, aziridinyl, azetidinyl, pyrrolidinyl, oxetanyl, tetrahydrofuranyl, morpholino, piperidinyl, and piperazinyl;

1.49 Compound 1.48, wherein $R^3$ is selected from H, F, Cl, Br, I, cyano, nitro, hydroxy, amino, methoxy, ethoxy, propoxy, isopropoxy, fluoromethoxy, difluoromethoxy, trifluoromethoxy, cyclopropoxy, cyclobutoxy, N-methylamino, N-ethylamino, N,N-dimethylamino, N,N-diethylamino, N-ethyl-N-methylamino, aziridinyl, azetidinyl, pyrrolidinyl, oxetanyl, tetrahydrofuranyl, morpholino, piperidinyl, and piperazinyl;

1.50 Compound 1.49, wherein $R^3$ is selected from hydroxy, amino, methoxy, ethoxy, fluoromethoxy, difluoromethoxy, trifluoromethoxy, N-methylamino, N-ethylamino, aziridinyl, azetidinyl, and oxetanyl;

1.51 Compound 1, or any of 1.1-1.50, wherein Ar is phenyl or 5- or 6-membered heteroaryl (e.g., thiophenyl, pyridyl), optionally substituted by 1-5 groups R;

1.52 Compound 1.51, wherein Ar is 5- or 6-membered heteroaryl (e.g., thiophenyl, pyridyl);

1.53 Compound 1.52, wherein Ar is selected from thiophenyl, furanyl, pyrrolyl, pyrazolyl, imidazolyl, thiazolyl, oxazolyl, isothiazolyl, and isoxazolyl;

1.54 Compound 1.52, wherein Ar is selected from pyridyl, pyrazinyl, pyridazinyl, and pyrimidinyl;

1.55 Compound 1.51, wherein Ar is phenyl;

1.56 Compound 1 or any of 1.51-1.55, wherein Ar is unsubstituted;

1.57 Compound 1, or any of 1.51-1.55, wherein Ar is a six-membered ring (e.g., phenyl or 6-membered heteroaryl) substituted by 1, 2, 3, 4, or 5 groups R;

1.58 Compound 1.57, wherein Ar is a six-membered ring (e.g., phenyl or 6-membered heteroaryl) substituted by 1, 2, or 3 groups R;

1.59 Compound 1.58, wherein Ar is phenyl substituted by 1, 2, or 3 groups R;

1.60 Compound 1.59, wherein Ar is phenyl substituted by 1 group R in the ortho, meta, or para position of the ring;

1.61 Compound 1.59, wherein Ar is phenyl substituted by 2 group R, wherein the two groups R are in the two ortho positions of the ring, or in one ortho and one para position of the ring, or in the two meta positions of the ring, or in one ortho and one meta position of the ring.

1.62 Compound 1.59, wherein Ar is phenyl substituted by 3 groups R, wherein the three groups R include at least one group in the para position of the ring, 1.63 Compound 1.62, wherein the three groups R are in the two ortho positions and the para position of the ring.

1.64 Compound 1, or any of 1.57-1.63, wherein the one or more groups R are each independently selected from halo (e.g., F, Cl, Br, I), cyano, nitro, hydroxy, amino, $C_{1-6}$ alkyl (e.g., methyl), $C_{3-6}$ cycloalkyl (e.g., cyclopropyl), $C_{1-6}$ haloalkyl (e.g., trifluoromethyl), $C_{1-6}$ alkoxy (e.g., methoxy), $C_{1-6}$haloalkoxy (e.g., trifluoromethoxy), $C_{3-6}$halocycloalkyl (e.g., 2,2-difluorocyclopropyl), NH($C_{1-6}$ alkyl) (e.g., N-methylamino), N($C_{1-6}$ alkyl)($C_{1-6}$ alkyl) (e.g., N,N-dimethylamino), and 3-6 membered heterocycloalkyl (e.g., azetidinyl, aziridinyl, oxetanyl), each of which is optionally substituted;

1.65 Compound 1.64, wherein the one or more groups R are each independently selected from halo (e.g., F, Cl, Br, I), cyano, nitro, hydroxy, $C_{1-6}$ haloalkyl (e.g., trifluoromethyl), $C_{1-6}$ haloalkoxy (e.g., trifluoromethoxy), and $C_{3-6}$halocycloalkyl (e.g., 2,2-difluorocyclopropyl), each of which is optionally substituted;

1.66 Compound 1.65, wherein the one or more groups R are each independently selected from halo (e.g., F, Cl, Br, I), cyano, nitro, $C_{1-6}$haloalkyl (e.g., trifluoromethyl), and $C_{1-6}$haloalkoxy (e.g., trifluoromethoxy), each of which is optionally substituted;

1.67 Compound 1.66, wherein the one or more groups R are each independently selected from halo (e.g., F, Cl, Br, I), cyano, nitro, $C_{1-3}$ haloalkyl (e.g., trifluoromethyl), and $C_{1-3}$haloalkoxy (e.g., trifluoromethoxy), each of which is optionally substituted;

1.68 Compound 1.67, wherein the one or more groups R are each independently selected from F, Cl, Br, I, cyano, nitro, trifluoromethyl, and trifluoromethoxy;

1.69 Compound 1.68, wherein the one or more groups R are each independently selected from F, Cl, Br, trifluoromethyl, and trifluoromethoxy;

1.70 Compound 1.69, wherein the one or more groups R are each independently selected from Cl, Br, trifluoromethyl, and trifluoromethoxy;

1.71 Compound 1.70, wherein the one or more groups R are each independently selected from Cl and trifluoromethyl;

1.72 Compound 1, or any of 1.57-1.71, wherein Ar is selected from 2,6-dichloro-4-trifluoromethylphenyl, 2,6-dichloro-4-trifluoromethoxyphenyl, 2,6-dichloro-4-bromophenyl, 2,6-dichloro-4-difluoromethylphenyl, 2,6-dichloro-4-difluoromethoxyphenyl, 2,6-dichloro-4-fluoromethylphenyl, 2,6-dichloro-4-fluoromethoxyphenyl, 2,6-dichloro-4-methylphenyl, 2,6-dichloro-4-methoxyphenyl, 2,4,6-trichlorophenyl, 2-chloro-4-trifluoromethoxyphenyl, 2-chloro-4-bromophenyl, 2-chloro-4-difluoromethylphenyl, 2-chloro-4-difluoromethoxyphenyl, 2-chloro-4-fluoromethylphenyl, 2-chloro-4-fluoromethoxyphenyl, 2-chloro-4-methylphenyl, 2-chloro-4-methoxyphenyl, 2,4-dichlorophenyl, and 2-chloro-4-bromophenyl;

1.73 Compound 1.72, wherein Ar is selected from 2,6-dichloro-4-trifluoromethylphenyl, and 2,6-dichloro-4-trifluoromethoxyphenyl;

1.74 Compound 1.73, wherein Ar is 2,6-dichloro-4-trifluoromethylphenyl;

1.75 Compound 1, or any of 1.1-1.74, wherein the Compound of Formula I is a Compound of Formula Ia:

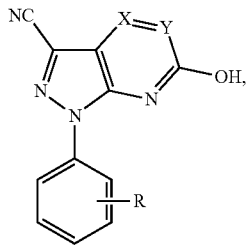

wherein X, Y, and R, are as defined in any preceding embodiment;

1.76 Compound 1, or any of 1.1-1.74, wherein the Compound of Formula I is a Compound of Formula Ib:

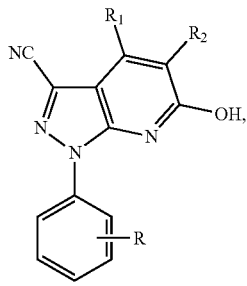

wherein $R^1$, $R^2$, and R, are as defined in any preceding embodiment;

1.77 Compound 1.76, wherein $R^1$ is selected from H, halo (e.g., F, Cl), cyano, nitro, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), and $C_{1-6}$ haloalkoxy (e.g., trifluoromethoxy), each of which is optionally substituted as defined herein; and $R^2$ is selected from H, halo (e.g., F, Cl), cyano, hydroxy, amino, $C_{1-6}$alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), $C_{1-6}$ haloalkoxy (e.g., trifluoromethoxy), and $C_{3-6}$ cycloalkoxy (e.g., cyclopropoxy), each of which is optionally substituted;

1.78 Compound 1.76, wherein $R^1$ is selected from halo (e.g., F, Cl), cyano, $C_{1-3}$ alkyl (e.g., methyl, ethyl), and $C_{1-3}$ haloalkyl (e.g., trifluoromethyl), each of which is optionally substituted as defined herein, and $R^2$ is selected from H, halo (e.g., F, Cl), cyano, hydroxy, $C_{1-3}$ alkyl (e.g., methyl, ethyl), $C_{1-3}$ haloalkyl (e.g., trifluoromethyl), $C_{1-3}$ alkoxy (e.g., methoxy, ethoxy), and $C_{1-6}$ haloalkoxy (e.g., trifluoromethoxy), each of which is optionally substituted;

1.79 Compound 1.76, wherein $R^1$ is selected from halo (e.g., F, Cl), cyano, $C_{1-3}$ alkyl (e.g., methyl, ethyl), and $C_{1-3}$ haloalkyl (e.g., trifluoromethyl), each of which is optionally substituted as defined herein, and $R^2$ is selected from H, halo (e.g., F, Cl), cyano, $C_{1-3}$ alkyl (e.g., methyl, ethyl), and $C_{1-3}$ haloalkyl (e.g., trifluoromethyl), each of which is optionally substituted;

1.80 Compound 1.76, wherein $R^1$ is selected from H, F, Cl, Br, I, cyano, methyl, ethyl, isopropyl, cyclopropyl, fluoromethyl, difluoromethyl, trifluoromethyl, methoxy, ethoxy, fluoromethoxy, difluoromethoxy, trifluoromethoxy, cyclopropoxy, azirdinyl, azetidinyl, and oxetanyl, and $R^2$ is selected from H, F, Cl, Br, I, cyano, hydroxy, amino, methyl, fluoromethyl, difluoromethyl, and trifluoromethyl;

1.81 Compound 1.76, wherein $R^1$ is selected from H, F, Cl, Br, I, cyano, methyl, fluoromethyl, difluoromethyl, and trifluoromethyl, and $R^2$ is selected from H, F, Cl, Br, and cyano;

1.82 Compound 1.76, wherein $R^1$ is $C_{1-3}$haloalkyl (e.g., trifluoromethyl) and $R^2$ is selected from H, F, Cl, Br, and cyano;

1.83 Compound 1.76, $R^1$ is selected from fluoromethyl, difluoromethyl, and trifluoromethyl, and $R^2$ is H;

1.84 Compound 1.76, wherein $R^1$ is selected from halo (e.g., F, Cl), cyano, $C_{1-3}$ alkyl (e.g., methyl, ethyl), $C_{3-6}$ cycloalkyl (e.g., cyclopropyl), and $C_{1-3}$ haloalkyl (e.g., trifluoromethyl), each of which is optionally substituted as defined herein; and $R^2$ is selected from H, halo (e.g., F, Cl), cyano, hydroxy, amino, $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), $C_{1-6}$ haloalkoxy (e.g., trifluoromethoxy), and $C_{3-6}$ cycloalkoxy (e.g., cyclopropoxy), each of which is optionally substituted;

1.85 Compound 1.76, wherein $R^1$ is selected from halo (e.g., F, Cl), cyano, $C_{1-3}$ alkyl (e.g., methyl, ethyl), $C_{3-6}$ cycloalkyl (e.g., cyclopropyl), and $C_{1-3}$ haloalkyl (e.g., trifluoromethyl), each of which is optionally substituted as defined herein; and $R^2$ is selected from H, halo (e.g., F, Cl), cyano, $C_{1-6}$ alkyl (e.g., methyl, ethyl), and $C_{1-6}$ haloalkyl (e.g., trifluoromethyl), each of which is optionally substituted;

1.86 Compound 1.76, wherein $R^1$ is selected from halo (e.g., F, Cl), cyano, $C_{1-3}$ alkyl (e.g., methyl, ethyl), $C_{3-6}$ cycloalkyl (e.g., cyclopropyl), and $C_{1-3}$ haloalkyl (e.g., trifluoromethyl), each of which is optionally substituted as defined herein; and $R^2$ is H;

1.87 Compound 1.76, wherein $R^1$ is selected from $C_{1-3}$ alkyl (e.g., methyl, ethyl), $C_{3-6}$ cycloalkyl (e.g., cyclopropyl), and $C_{1-3}$ haloalkyl (e.g., trifluoromethyl), each of which is optionally substituted as defined herein; and $R^2$ is H;

1.88 Compound 1.76, wherein $R^1$ is $C_{1-3}$ alkyl (e.g., methyl, ethyl); and $R^2$ is H;

1.89 Compound 1.76, wherein $R^1$ is $C_{3-6}$ cycloalkyl (e.g., cyclopropyl); and $R^2$ is H;

1.90 Compound 1.76, wherein $R^1$ is $C_{1-3}$ haloalkyl (e.g., trifluoromethyl); and $R^2$ is H;

1.91 Compound 1.76, wherein $R^1$ is selected from methyl, ethyl, isopropyl, $d_3$-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl; and $R^2$ is H;

1.92 Compound 1.76, wherein $R^1$ is selected from methyl, isopropyl, d-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl; and $R^2$ is H;

1.93 Compound 1.76, wherein $R^1$ is selected from methyl, isopropyl, $d_3$-methyl, and cyclopropyl; and $R^2$ is H;

1.94 Compound 1.76, wherein R is selected from, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl; and $R^2$ is H;

1.95 Compound 1.76, wherein $R^1$ is difluoromethyl; and $R^2$ is H;

1.96 Compound 1, or any of 1.1-1.74, wherein the Compound of Formula I is a Compound of Formula Ic:

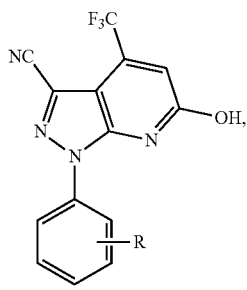

wherein R is as defined in any preceding embodiment;

1.97 Any of Compounds 1.75-1.96, wherein there are one, two or three groups R, each independently selected from halo (e.g., F, Cl, Br, I), cyano, nitro, hydroxy, $C_{1-6}$ haloalkyl (e.g., trifluoromethyl), $C_{1-6}$ haloalkoxy (e.g., trifluoromethoxy), and $C_{3-6}$ halocycloalkyl (e.g., 2,2-difluorocyclopropyl);

1.98 Any of Compounds 1.75-1.96, wherein there are one, two or three groups R, each independently selected from halo (e.g., F, Cl, Br, I), cyano, nitro, $C_{1-6}$ haloalkyl (e.g., trifluoromethyl), and $C_{1-3}$ haloalkoxy (e.g., trifluoromethoxy);

1.99 Any of Compounds 1.75-1.96, wherein there are one, two or three groups R, each independently selected from halo (e.g., F, Cl, Br, I), cyano, nitro, $C_{1-3}$ haloalkyl (e.g., trifluoromethyl), and $C_{1-3}$ haloalkoxy (e.g., trifluoromethoxy);

1.100 Any of Compounds 1.75-1.96, wherein there are one, two or three groups R, each independently selected from F, Cl, Br, I, cyano, nitro, trifluoromethyl, and trifluoromethoxy;

1.101 Any of Compounds 1.75-1.96, wherein there are one, two or three groups R, each independently selected from Cl, Br, trifluoromethyl, and trifluoromethoxy;

1.102 Any of Compounds 1.75-1.96, wherein there are one, two or three groups R, each independently selected F, Cl, and trifluoromethyl, and trifluoromethoxy;

1.103 Any of Compounds 1.75-1.96, wherein there are one, two or three groups R, each independently selected Cl, and trifluoromethyl;

1.104 Any of Compounds 1.97-1.103, wherein there are two or three groups R;

1.105 Any of Compounds 1.97-1.103, wherein there are three groups R;

1.106 Compound 1, or any of 1.1-1.105, wherein the Compound of Formula I is:

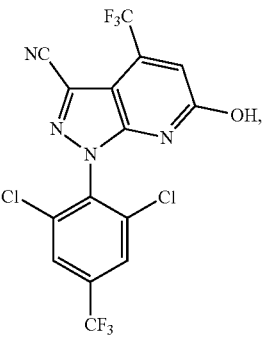 [SMILES: N#Cc1nn(-c2c(Cl)cc(C(F)(F)F)cc2Cl)c2nc(O)cc(C(F)(F)F)c12]

in free or salt form;

1.107 Compound 1, or any of 1.1-1.105, wherein the Compound of Formula I is a Compound of Formula Id:

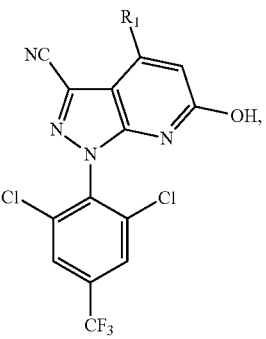

in free or salt form, wherein $R^1$ is as defined in any preceding embodiment, e.g., wherein $R^1$ is selected from H, halo, cyano, nitro, hydroxy, amino, $C_{1-6}$ alkyl, $C_{3-6}$ cycloalkyl, $C_{1-6}$ haloalkyl, $C_{1-6}$ alkoxy, $C_{1-6}$ haloalkoxy, $C_{3-6}$ cycloalkoxy, $C_{3-6}$ halocycloalkyl, NH($C_{1-6}$ alkyl) N($C_{1-6}$ alkyl)($C_{1-6}$ alkyl), and 3-6 membered heterocycloalkyl, each of which is optionally substituted;

1.108 Compound 1.107, wherein $R^1$ is selected from H, halo (e.g., F, Cl), cyano, nitro. $C_{1-6}$ alkyl (e.g., methyl, ethyl), $C_{3-6}$ cycloalkyl (e.g., cyclopropyl), $C_{1-6}$ haloalkyl (e.g., trifluoromethyl), $C_{1-6}$ alkoxy (e.g., methoxy, ethoxy), and $C_{1-6}$ haloalkoxy (e.g., trifluoromethoxy), each of which is optionally substituted as defined herein;

1.109 Compound 1.107, wherein $R^1$ is selected from halo (e.g., F, Cl), cyano, $C_{1-3}$ alkyl (e.g., methyl, ethyl), $C_{3-6}$ cycloalkyl (e.g., cyclopropyl), and $C_{1-6}$ haloalkyl (e.g., trifluoromethyl), each of which is optionally substituted as defined herein;

1.110 Compound 1.107, wherein $R^1$ is selected from halo (e.g., F, Cl), cyano, $C_{1-3}$ alkyl (e.g., methyl, ethyl), $C_{3-6}$ cycloalkyl (e.g., cyclopropyl), and $C_{1-3}$ haloalkyl (e.g., trifluoromethyl);

1.111 Compound 1.107, wherein $R^1$ is selected from $C_{1-3}$ alkyl (e.g., methyl, ethyl), $C_{3-6}$ cycloalkyl (e.g., cyclopropyl), and $C_{1-3}$ haloalkyl (e.g., trifluoromethyl);

1.112 Compound 1.107, wherein $R^1$ is $C_{1-3}$ alkyl (e.g., methyl, ethyl);

1.113 Compound 1.107, wherein $R^1$ is $C_{3-6}$ cycloalkyl (e.g., cyclopropyl);

1.114 Compound 1.107, wherein $R^1$ is $C_{1-3}$ haloalkyl (e.g., trifluoromethyl);

1.115 Compound 1.107, wherein $R^1$ is selected from methyl, ethyl, isopropyl, $d_3$-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1-difluoroethyl;

1.116 Compound 1.107, wherein $R^1$ is selected from methyl, isopropyl, $d_3$-methyl, cyclopropyl, fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl;

1.117 Compound 1.107, wherein $R^1$ is selected from methyl, isopropyl, $d_3$-methyl, and cyclopropyl;

1.118 Compound 1.107, wherein $R^1$ is selected from fluoromethyl, difluoromethyl, trifluoromethyl, chloromethyl, dichloromethyl, trichloromethyl, chlorofluoromethyl, chlorodifluoromethyl, bromodifluoromethyl, and 1,1-difluoroethyl;

1.119 Compound 1, or any of 1.1-1.118, wherein the compound of Formula I is:

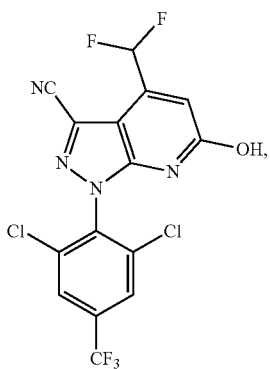 [SMILES: N#Cc1nn(-c2c(Cl)cc(C(F)(F)F)cc2Cl)c2nc(O)cc(C(F)F)c12]

in free or salt form;

1.120 Compound 1, or any of 1.1-1.118, wherein the compound of Formula I is selected from the group consisting of:

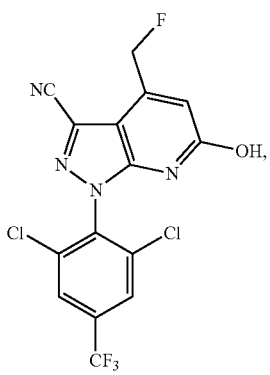

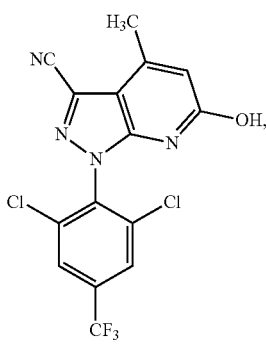

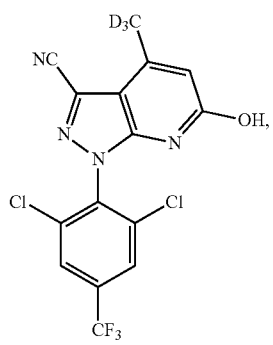

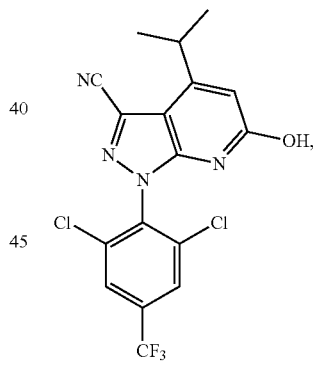

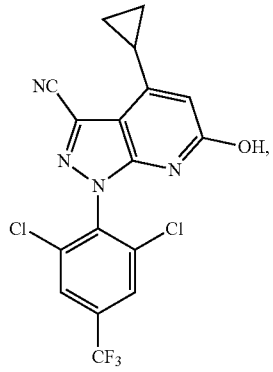

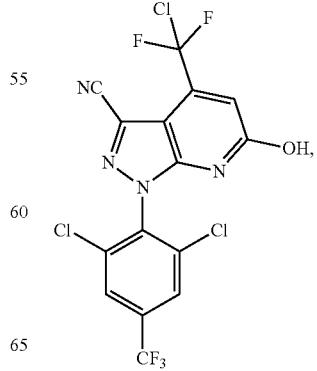

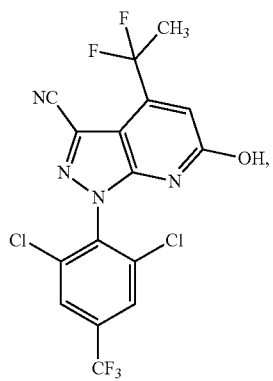

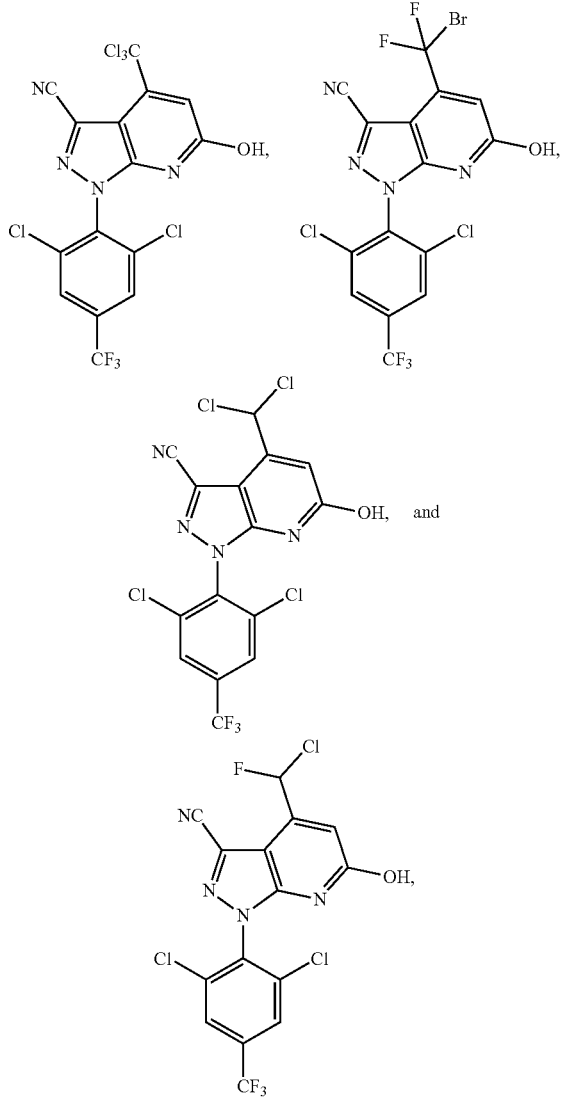

each in free or salt form;

1.121 Compound 1, or any of 1.1-1.120, wherein the Compound of Formula T is free (I.e., free base) form;

1.122 Compound 1, or any of 1.1-1.121, wherein the Compound of Formula I is in salt form, e.g., acid addition salt form or base addition salt form, 1.123 Compound 1.122, wherein the acid addition salt form is selected from a hydrochloride, hydrobromide, sulfate, phosphate, nitrate, acetate, propionate, benzoate, mesylate, besylate, tosylate, citrate, fumarate, glycolate, gluconate, tartrate, malate, maleate, succinate, or oxalate salt;

1.124 Compound 1.122, wherein the base addition salt is select from a lithium, sodium, potassium, magnesium, calcium, or aluminum salt;

1.125 Compound 1, or any of 1.1-1.124, wherein the compound is intended for use to treat, control, suppress, or eradicate, an infection or infestation of an insect (arthropod), such as an adult insect, insect egg, insect larva, insect nymph, and/or insect pupa;

1.126 Compound 1.125, wherein the insect is selected from one or more of the following: fleas, lice, ticks, mites, mosquitos, grasshopper, locust, beetles (such as cane beetles, thrips, stink bugs, boxelders, Japanese beetles, emerald ash borer), ants (such as carpenter ants, fire ants), cockroaches, termites, flies, aphids, moths, butterflies, and wasps;

1.127 Compound 1.26, wherein the insect is selected from one or more of the following:

Acarina, including ticks (e.g., *Ixodes* spp., *Boophilus* spp. e.g., *Boophilus microplus*, *Amblyomnma* spp., *Hyalomma* spp., *Rhipicephalus* spp. e.g., *Rhipicephalus appendiculatus*, *Haemaphysalis* spp., *Dermacentor* spp. *Ornithodorus* spp. (e.g., *Ornithodorus moubata*), and mites (e.g., *Damalinia* spp., *Dermanyssus gallinae*, *Sarcoptes* spp. e.g., *Sarcoptes scabiei*, *Psoroptes* spp., *Chorioptes* spp., *Demodex* spp., *Eutrombicula* spp., *Tetranychus* spp., *Panonychus* spp. and *Bryobia* spp. (spider maites), *Eriophyes* spp. (gall mites), *Polyphacotarsonemus* spp.;

Chilpoda (centipedes), including *Scutigeromorpha* (e.g., *Scutigera* spp)

Diplopoda (millipedes), including Julida, e.g., *Blaniulus* spp.,

Symphyla (pseudocentipedes), including *Scutigerella* spp., *Symphylella* spp., *Henseniella* spp., Isopoda, including *Oniscus* spp. (woodlice));

Diptera (flies, including mosquitos), e.g., *Aedes* spp., *Anopheles* spp., *Culex* spp., *Musca* spp., *Hypoderma* spp., *Gasterophilus* spp., *Simulium* spp, *Hylemyia* spp. (root flies), *Atherigona* spp. and *Chlorops* spp. (shoot flies), *Phytomyza* spp. (leaf miners), *Ceratitis* spp. (fruit flies);

Hemiptera (true bugs), e.g., *Triatoma* spp., *Psylla* spp., *Bemisia* spp., *Trialeurodes* spp., *Aphis* spp., *Myzus* spp., *Megoura viciae*, *Phylloxera* spp., *Adelges* spp., *Phorodon humuli* (hop damson aphid), *Aeneolamia* spp., *Nephotettix* spp. (rice leafhoppers), *Empoasca* spp., *Nilaparvata* spp., *Perkinsiella* spp., *Pyrilla* spp., *Aonidiella* spp. (red scales), *Coccus* spp., *Pseucoccus* spp., *Helopeltis* spp. (mosquito bugs), *Lygus* spp., *Dysdercus* spp., *Oxycarenus* spp., and *Nezara* spp.;

Phthiraptera (louses) (e.g., *Damalinia* spp., *Linognathus* spp.);

Siphonaptera (fleas), e.g., *Ctenocephalides* spp., *Tunga* spp., *Ceratophyllus* spp.;

Blattodea (cockroaches), e.g., *Periplaneta* spp., *Blattella* spp.;

Hymenoptera (sawflies, wasps, ants), e.g., *Athalia* spp., *Cephus* spp. (saw flies), *Atta* spp. (leaf cutting ants), *Vespula* spp., *Dolichovespula* spp., *Vespa* spp., *Linepithema* spp., *Solenopsis* spp., *Anoplolepis* spp., *Camponotus* spp., *Formica* spp., *Myrmica* spp., and *Monomorium* spp., e.g., *Monomorium plaraonis;*

Coleoptera (beetles), including *Ephestia* spp. (flour moths), *Anthrenus* spp. (carpet beetles), *Tribolium* spp. (flour beetles), *Sitophilus* spp. (grain weevils), e.g., *Hypothenemus hampei* (coffee berry borer), *Hylesinus* spp. (bark beetles), *Anthonomus grandis* (cotton boll weevil), *Acalymma* spp. (cucumber beetles), *Lema* spp., *Psylliodes* spp., *Leplinotarsa decemlineata* (Colorado potato beetle), *Diabrotica* spp. (corn rootworms), *Gonocephalum* spp. (false wire worms), *Agriotes* spp. (wireworms), *Dermolepida* and *Heteronychus* spp. (white grubs), *Phaedon cochleariae* (mustard beetle), *Lissorhoptrus oryzophilus* (rice water weevil), *Melioethes* spp.

(pollen beetles), *Ceutorhynchus* spp., *Rhynchophorus* and *Cosmopolites* spp. (root weevils);

Lepidoptera (butterflies and moths, including their caterpillars and worms), e.g., *Heliothis* spp. such as *Heliothis virescens* (tobacco budworm), *Heliothis armioera* and *Heliothis zea, Spodoptera* spp. such as *S. exempta, S. littoralis* (Egyptian cotton worm), *S. eridania* (southern army worm), *Mamestra configurata* (bertha army worm); *Earias* spp. e.g., *P. insulana* (Egyptian bollworm), *Pectinophora* spp. e.g., *Pectinophora gossypiella* (pink bollworm), *Ostrinia* spp. such as *O. nubilalis* (European cornborer), *Trichoplusia ni* (cabbage looper), *Pieris* spp. (cabbage worms), *Laphyqma* spp. (army worms), *Agrotis* and *Amathes* spp. (cutworms), *Wiseana* spp. (porina moth), *Chilo* spp. (rice stein borer), *Tryporyza* spp. and *Diatraea* spp. (sugar cane borers and rice borers), *Sparganothis pilleriana* (grape berry moth), *Cydia pomonella* (codling moth), *Archips* spp. (fruit tree tortrix moths), and *Plutella* spp., e.g., *Plutella xylostella* (diamond back moth);

Thysanoptera (thrips), such as *Anaphothrips* spp., *Megalurothrips* spp., *Scirtothrips* spp., *Sorgothrips* spp., *Frankiniella* spp., and *Thrips* spp., e.g., *Thrips tabaci;*

Orthoptera such as *Locusta* and *Schistocerca* spp. (locusts) and crickets e.g., *Gryllus* spp. and *Acheta* spp.;

Collembola (springtails), e.g., *Sminthurus* spp. and *Onychiurus* spp.;

Isoptera and Neoisoptera (termites), e.g., *Odontotermes* spp., *Reticulitermes* spp., *Heterotermes* spp., *Coptotermes* spp.; and Dermaptera (earwigs), e.g., *Forficula* spp.;

1.128 Compound 1.127, wherein the insect is the poultry mite or red mite, *Dermanyssus gallinae;*

1.129 Compound 1.128, wherein the compound is administered to chickens or applied to chicken coops, chicken pens, chicken cages, other chicken enclosures, chicken farms, or chicken feed;

1.130 Compound 1, or any of 1.1-1.129, wherein the compound is intended for use to treat, control, suppress, or eradicate, an infection or infestation of an insect (arthropod), such as an adult insect, insect egg, insect larva, insect nymph, and/or insect pupa, wherein the insect is selected from one or more of fleas, ticks, mites, lice, fire ants, termites, beetles, cockroaches, mole crickets, thrips, rootworms, and weevils.

In a second aspect, the present disclosure also provides a pharmaceutical or insecticidal composition (Composition 1) comprising an effective amount of a Compound of Formula I, or any of 1.1-1.130, in free or salt form, in admixture with a pharmaceutically acceptable or insecticidally acceptable diluent or carrier.

In further embodiments of the second aspect, the present disclosure provides:

1.1 A pharmaceutical composition comprising a therapeutically effective amount of any one of Compounds 1.1-1.130, and at least one pharmaceutically acceptable diluent or carrier;

1.2 Composition 1.1, wherein the pharmaceutical composition is formulated for administration to a human patient;

1.3 Composition 1.1, wherein the pharmaceutical composition is formulated for administration to an animal patient (e.g., a veterinary composition);

1.4 Composition 1.3, wherein the animal is a livestock animal, such as a chicken, turkey, geese, duck, pig, cattle, goat, or sheep;

1.5 Composition 1.4, wherein the compound does not bioaccumulate in the livestock animal, 1.6 Composition 1.4 or 1.5, wherein the compound does not accumulate in livestock animal food products (e.g., meat, such as beef, poultry, pork, or eggs);

1.7 Composition 1.6, wherein said food products comprise less than 5 ppm of the compound, e.g., less than 4 ppm, or less than 3 ppm, or less than 2 ppm, or less than 1 ppm, or less than 0.5 ppm or less than 0.1 ppm;

1.8 Composition 1.3, wherein the animal is a non-livestock work animal, such as a horse, donkey, mule, ox, llama, or camel;

1.9 Composition 1.3, wherein the animal is a companion animal, such as a dog, cat, rabbit, ferret, rat, or mouse;

1.10 Any of Compositions 1.1-1.9, wherein the composition is formulated for oral administration to the human or animal, e.g., as a tablet, capsule, liquid solution, oral gel, powder, oral spray, feed additive, edible bait, salt lick, or dietary supplement;

1.11 Any of Compositions 1.1-1.9, wherein the composition is formulated for transdermal administration to the human or animal, for systemic delivery, e.g., as a liquid solution, gel, or patch;

1.12 Any of Compositions 1.1-1.9, wherein the composition is formulated for topical administration to the human or animal, such as to the skin, hair, or fur, for local (non-systemic) delivery, e.g., as a liquid solution, spray, gel (e.g., for "spot-on" application), cream, ointment, shampoo, foam, bath, or dip;

1.13 Any of Compositions 1.3-1.9, wherein the composition is formulated for administration to the animal using a removable collar worn by the animal around the neck;

1.14 Any of Compositions 1.1-1.9, wherein the composition is formulated for administration to the human or animal as a rapid-acting injection, such as an intravenous, subcutaneous, intramuscular, or intraperitoneal injection to provide immediate release of the compound to the animal;

1.15 Any of Compositions 1.1-1.9, wherein the composition is formulated for administration to the human or animal as a long-acting injection, such as a subcutaneous, intramuscular or intraperitoneal injection using a sustained or delayed release vehicle (e.g., a polymer matrix), e.g., to provide sustained or delayed release of a therapeutically effective amount of the Compound over a period of time, for example, 1 week to 1 month, or 1 month to 3 months, or 3 months to 6 months;

1.16 An insecticidal composition comprising an insecticidally effective amount of any one of Compounds 1.1-1.130, and at least one insecticidally acceptable diluent or carrier;

1.17 Composition 1.16, wherein the composition is formulated for application to plants or to media in which plants grow, e.g., for application to agricultural crops, agricultural fields, orchards, vineyards, plantations, or soil for agricultural use;

1.18 Composition 1.17, wherein the plant or crop is selected from rice, corn, wheat, sugarcane, potato, rye, oats, barley, millet, soybean, cotton, vegetables (e.g., beans, lettuce, onions, tomatoes, peppers), fruits and nuts (e.g., grapes, apples, citrus, banana, kiwi, avocado, mango, olive, walnut, peanut), tea, coffee, tobacco, and cocoa;

1.19 Composition 1.16, wherein the composition is formulated for application to ornamental plants, such as in residential or commercial greenhouses, gardens, or lawns;

1.20 Composition 1.16, wherein the composition is formulated for residential or commercial use, e.g., for application to homes, apartment buildings, office buildings, manufacturing facilities, hotels, motels, parks, sporting facilities (e.g., athletic stadiums, golf courses), and other public spaces;

1.21 Composition 1.20, wherein the composition is formulated for application to stored food products (e.g., grains, fruits, nuts, spices, tobacco), clothing, bedding, furniture, carpets, rugs, and other household items;

1.22 Any one of Compositions 1.16-1.21, wherein the composition is formulated for application by aerosol spray, e.g., as suspension of solid or liquid particles having a size of less than one micron;

1.23 Any one of Compositions 1.16-1.21, wherein the composition is formulated for application by liquid spray (e.g., a mist of liquid droplets having a droplet size of greater than one micron);

1.24 Any one of Compositions 1.16-1.21, wherein the composition is a dry formulation, such as a dust, wettable powder, granule, tablet, or water dispersible granule, for example, formulated for application by dusting (e.g., a mist of solid particles having a particle size of greater than one micron), sprinkling, spreading, or as a bulk liquid, fog, lacquer, paint, or smoke;

1.25 Composition 1, or any of 1.1-1.24, wherein the composition is intended for use to treat, control, suppress, or eradicate, an infection or infestation of an insect (arthropod), such as an adult insect, insect egg, insect larva, insect nymph, and/or insect pupa;

1.26 Composition 1.25, wherein the insect is selected from one or more of the following: fleas, lice, ticks, mites, mosquitos, grasshopper, locust, beetles (such as cane beetles, thrips, stink bugs, boxelders, Japanese beetles, emerald ash borer), ants (such as carpenter ants, fire ants), cockroaches, termites, flies, aphids, moths, butterflies, and wasps;

1.27 Composition 1.25, wherein the insect is selected from one or more of the following: or example:

*Acarina* (e.g., ticks and mites, such as of the superorders Parasitiformes and Acariformes, and the orders Ixodida, Mesostigmata, Sarcoptiformes, and Trombidiformes), including ticks (e.g., *Ixodes* spp., *Boophilus* spp. e.g., *Boophilus microplus*, *Amblyomma* spp., *Hyalomma* spp., *Rhipicephalus* spp. e.g., *Rhipicephalus appendiculatus*, *Haemaphysalis* spp., *Dermacentor* spp., *Ornithodorus* spp. (e.g., *Ornithodorus moubata*), and mites (e.g., *Dermanyssus* spp., e.g., *Dermanyssus gallinae*, *Ornithonyssus* spp., e.g., *Ornithonyssus sylviarum*, *galinae*, *Sarcoptes* spp. e.g., *Sarcoptes scabiei*, *Psoroptes* spp., *Chorioptes* spp., *Demodex* spp., *Eutrombicula* spp., *Tetranychus* spp., *Panonychus* spp. and *Bryobia* spp. (spider mites), *Eriophyes* spp. (gall mites), Polyphagotarsonemus spp., *Varroa* spp., e.g., *Varroa destructor*;

Psocodea (lice), including Anoplura (e.g., *Pediculus* spp., *Pthirus* spp.), Ischonocera (e.g., *Bovicola* spp., *Damalinia* spp., *Felicola* spp., *Saemundssonia* spp., *Trichodectes* spp.), and Amblycera (e.g., *Holomenopon* spp., *Menopon* spp., e.g., *Menopon gallinae*, *Menecanthus* spp., e.g., *Menecanthus stramineus*, *Heterodoxus* spp., e.g., *Heterodoxus spiniger*);

Chilpoda (centipedes), including *Scutigeromorpha* (e.g., *Scutigera* spp.);

Diplopoda (millipedes), including Julida, e.g., *Blaniulus* spp.;

Symphyla (pseudocentipedes), including *Scutigerella* spp., *Symphylella* spp., *Henseniella* spp.;

Isopoda, including *Oniscus* spp. (woodlice));

Diptera (flies, including mosquitos), e.g., *Aedes* spp., *Anopheles* spp., *Culex* spp., *Musca* spp., *Hypoderma* spp., *Gasterophilus* spp., *Simulium* spp., *Hylemyia* spp. (root flies), *Atherigona* spp. and *Chlorops* spp. (shoot flies), *Phytomyza* spp. (leaf miners), *Ceratitis* spp. (fruit flies);

Hemiptera (true bugs), e.g., *Triatoma* spp., *Psylla* spp., *Bemisia* spp., *Trialeurodes* spp., *Aphis* spp., *Myzus* spp., *Megoura viciae*, *Phylloxera* spp., *Adelges* spp., *Phorodon humuli* (hop damson aphid), *Aeneolamia* spp., *Nephotettix* spp. (rice leafhoppers), *Empoasca* spp., *Nilaparvata* spp., *Perkinsiella* spp., *Pyrilla* spp., *Aonidiella* spp. (red scales), *Coccus* spp., *Pseucoccus* spp., *Helopeltis* spp. (mosquito bugs), *Lygus* spp., *Dysdercus* spp., *Oxycarenus* spp., and *Nezara* spp.;

Phthiraptera (louses) (e.g., *Damalinia* spp., *Linognathus* spp.);

Siphonaptera (fleas), e.g., *Ctenocephalides* spp., *Tunga* spp., *Ceratophyllus* spp.;

Blattodea (cockroaches), e.g., *Periplaneta* spp., *Blatella* spp.;

Hymenoptera (sawflies, wasps, ants), e.g., *Athalia* spp., *Cephus* spp. (saw flies), *Atta* spp. (leaf cutting ants), *Vespula* spp., *Dolichovespula* spp., *Vespa* spp., *Linepithema* spp., *Solenopsis* spp., *Anoplolepis* spp., *Camponotus* spp., *Formica* spp, *Myrmica* spp., and *Monomorium* spp., e.g., *Monomorium pharaonis*;

Coleoptera (beetles), including *Ephestia* spp. (flour moths), *Anthrenus* spp. (carpet beetles), *Tribolium* spp. (flour beetles), *Sitophilus* spp. (grain weevils), e.g., *Hypothenemus hampei* (coffee berry borer), *Hylesinus* spp. (bark beetles), *Anthonomus grandis* (cotton boll weevil), *Acalymma* spp. (cucumber beetles), *Lema* spp., *Psylliodes* spp., *Leptinotarsa decemlineata* (Colorado potato beetle), *Diabrotica* spp. (corn rootworms), *Gonocephalum* spp. (false wire worms), *Agriotes* spp. (wireworms), *Dermolepida* and *Heteronychus* spp. (white grubs), *Phaedon cochleariae* (mustard beetle), *Lissorhoptrus oryzophilus* (rice water weevil), *Melioethes* spp. (pollen beetles), *Ceutorhynchus* spp., *Rhynchophorus* and *Cosmopolites* spp. (root weevils);

Lepidoptera (butterflies and moths, including their caterpillars and worms), e.g., *Heliothis* spp. such as *Heliothis virescens* (tobacco budworm), *Heliothis armioera* and *Heliothis zea*, *Spodoptera* spp. such as *S. exempta*, *S. littoralis* (Egyptian cotton worm), *S. eridania* (southern army worm), *Mamestra configurata* (bertha army worm); *Earias* spp. e.g., *E. insulana* (Egyptian bollworm), *Pectinophora* spp. e.g., *Pectinophora gossypiella* (pink bollworm), *Ostrinia* spp. such as *O. nubilalis* (European cornborer), *Trichoplusia* n (cabbage looper), *Pieris* spp. (cabbage worms), *Laphyqma* spp. (army worms), *Agrotis* and *Amathes* spp. (cutworms), *Wiseana* spp. (porina moth), *Chilo* spp. (rice stein borer), *Tryporyza* spp. and *Diatraea* spp. (sugar cane borers and rice borers), *Sparganothis pilleriana* (grape berry moth), Cydia pomonella (codling moth), Archips spp. (fruit tree tortrix moths), and Plutella spp., e.g., Plutella xylostella (diamond back moth);

Thysanoptera (thrips), such as Anaphothrips spp., Megalurothrips spp., Scirtothrips spp., Sorgothrips spp., Frankiniella spp., and Thrips spp., e.g., Thrips tabaci;

Orthoptera such as Locusta and Schistocerca spp. (locusts) and crickets e.g., Gryllus spp. and Acheta spp.;

Collembola (springtails), e.g., Sminthurus spp. and Onychiurus spp.;

Isoptera and Neoisoptera (termites), e.g., Odontotermes spp., Reticulitermes spp., Heterotermes spp., Coptotermes spp.; and Dermaptera (earwigs), e.g., Forficula spp.;

1.28 Composition 1.25, wherein the insect is a mite of the superorder Parasitiformes, e.g., a mite of the order Mesostigmata, such as a mite of the family Dermanyssidae or Macronyssidae, such as a mite of the genus Dermanyssus (e.g. Dermanyssus gallinae) or Ornithonyssus (e.g., Ornithonyssus sylviarum), in particular the poultry mite or red mite, Dermanyssus gallinae;

1.29 Composition 1, or any of 1.1-1.28, wherein the composition further comprises one or more other insecticidal agents;

1.30 Composition 1.29, wherein the one or more other insecticidal agents are selected from: phenylpyrazoles, pyrethroids, neonicotinoids, organochlorines, organophosphates, butenolides, carbamates, and diamides (Ryanoids);

1.31 Composition 1.29, wherein the one or more other insecticidal agents are selected from fipronil, acetoprole, ethiprole, flufiprole, pyraclofos, pyrafluprole, pyriprole, pyrolan, and vanilliprole, allethrin, bifenthrin, cyfluthrin, cypermethrin, cyphenothrin, deltamethrin, dimefluthrin, esfenvalerate, etofenprox, fenpropathrin, fenvalerate, flucythrinate, flumethrin, imiprothrin, cyhalothrin (e.g., lambda cyhalothrin), metofluthrin, permethrin, phenothrin, prallethrin, resmethrin, silafluofen, fluvalinate (e.g., tau fluvalinate), tefluthrin, tetramethrin, tralomethrin, transfluthrin, acetamiprid, clothiandin, dinotefuran, imidacloprid, nitenpyram, nithiazine, thiacloprid, thiamethoxam, aldrin, chlordane, dieldrin, endosulfan, endrin, heptachlor, azamethiphos, azinphos methyl, chlorpyrifos, diazinon, dichlorvos, fenitrothion, malathion, parathion, parathion methyl, phosmet, terbufos, tetrachlorvinphos, flupyradifurone, aldicarb, bendiocarb, carbofuran, carbaryl, ethienocarb, fenobucarb, oxamyl, methomyl, and chlorantraniliprole;

1.32 Composition 1 or any of 1.1-1.31, wherein the composition is an aqueous solution, optionally comprising an organic co-solvent (e.g., methanol, ethanol, isopropanol, methoxymethanol, ethoxyethanol, 2-butoxyethanol), 1.33 Composition 1.32, wherein the composition is a solution comprising 2-butoxyethanol, ethanol and water;

1.34 Composition 1.33, wherein the composition is a solution comprising 2-butoxyethanol, ethanol, and water in a 7:2:1 v/v ratio, e.g., the composition comprises the Compound of Formula I dissolved, dispersed, or suspended in the solution comprising 2-butoxyethanol, ethanol, and water in a 7:2:1 v/v ratio;

1.35 Composition 1.32, wherein the composition is a solution comprising ethanol and water;

1.36 Composition 1.35, wherein the solution comprises ethanol and water in an about 75:25 to 99:1 v/v ratio, e.g., 75:25 to 95:5, or 75:25 to 90:10, or 75:25 to 85:15, or 75:25 to 80:20, or 80:20 to 99:1, or 80:20 to 95:5, or 80:20 to 90:10, or 80:20 to 85:15, or 85:15 to 99:1, or 85:15 to 95:5, or 85:15 to 90:10, or 90:10 to 99:1, or 90:10 to 95:5, or 95:5 to 99:1, or about 80:20, or about 85:15, or about 90:10, or about 95:5, or about 99:1, v/v;

1.37 Composition 1 or any of 1.1-1.31, wherein the composition is an aqueous suspension, optionally comprising an organic co-solvent (e.g., methanol, ethanol, isopropanol, methoxymethanol, ethoxyethanol, 2-butoxyethanol);

1.38 Composition 1.37, wherein the composition is a suspension comprising 2-butoxyethanol, ethanol and water;

1.39 Composition 1.38, wherein the composition is a suspension comprising 2-butoxyethanol, ethanol, and water in a 7:2:1 v/v ratio, e.g., the composition comprises the Compound of Formula I dissolved, dispersed, or suspended in the solution comprising 2-butoxyethanol, ethanol, and water in a 7:2:1 v/v ratio;

1.40 Composition 1.37, wherein the composition is a suspension comprising ethanol and water;

1.41 Composition 1.40, wherein the suspension comprises ethanol and water in an about 1:99 to 75:25 v/v ratio, e.g., 10:90 to 75:25, or 20:80 to 75:25, or 30:70 to 75:25, or 40:60 to 75:35, or 50:50 to 75:25, or 55:45 to 75:25, or 60:40 to 75:25, or 65:35 to 75:25, or 70:30 to 75:25, v/v;

1.42 Composition 1 or any of 1.1-1.41, wherein the composition comprises the Compound of Formula I in an amount of 0.1 to 1.0%, e.g., 0.1 to 0.5%, or 0.2 to 0.3%, or about 0.25%, w/v;

1.43 Composition 1 or any of 1.1-1.41, wherein the composition is a concentrate, which comprises the Compound of Formula I in an amount of 1 to 20%, e.g., 1 to 15%, or 1 to 10%, or 1 to 5% w/v;

1.44 Composition 1 or any of 1.1-1.43, wherein the composition comprises the Compound of Formula I of the following formula:

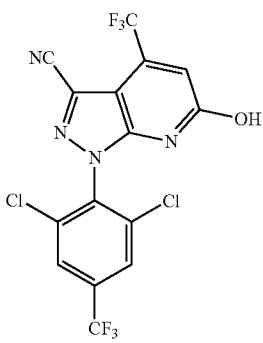 [SMILES: N#Cc1nn(-c2c(Cl)cc(C(F)(F)F)cc2Cl)c2nc(O)cc(C(F)(F)F)c12]

in free or salt form;

1.45 Composition 1 or any of 1.1-1.44, wherein the composition is formulated for delivery by spray (e.g., liquid spray or aerosol spray);

1.46 Composition 1 or any of 1.1-1.45, intended for use to treat, control, suppress, or eradicate, an infection or infestation of an insect (arthropod), such as an adult insect, insect egg, insect larva, insect nymph, and/or insect pupa, wherein the insect is the poultry mite or red mite, Dermanyssus gallinae;

1.47 Composition 1 or any of 1.1-1.46, wherein the composition is administered to chickens or applied to chicken coops, chicken pens, chicken cages, other chicken enclosures, chicken farms, or chicken feed;

1.48 Composition 1 or any of 1.1-1.45, intended for use to treat, control, suppress, or eradicate, an infection or infestation of an insect (arthropod), such as an adult insect, insect egg, insect larva, insect nymph, and/or insect pupa, wherein the insect is selected from one or more of fleas, ticks, mites, lice, fire ants, termites, beetles, cockroaches, mole crickets, thrips, rootworms, and weevils.

In a third aspect, the present disclosure provides a method (Method 1) for the treatment, control, suppression, or eradication, of an infection or infestation of an insect (arthropod), such as an adult insect, insect egg, insect larva, insect nymph, and/or insect pupa, comprising administering or applying an effective amount of a Compound of Formula I, or any of 1.1-1.130, in free or salt form, or a pharmaceutical Composition 1 or any of 1.1-1.48, to an animal or human patient in need thereof, or comprising applying a Compound of Formula I, or any of 1.1-1.130, or an insecticidal Composition 1 or any of 1.1-1.48, to a product or location in need thereof.

In further embodiments of the third aspect the present disclosure provides:

1.1 A method for the treatment, control, suppression, or eradication, of an infection or infestation of an insect (arthropod), such as an adult insect, insect egg, insect larva, insect nymph, and/or insect pupa, comprising administering or applying an effective amount of a Compound of Formula I, or any of 1.1-1.130, or a pharmaceutical Composition 1 or any of 1.1-1.48, to an animal or human patient in need thereof.

1.2 Method 1.1, wherein the patient is a human patient;

1.3 Method 1.1, wherein the patient is an animal patient (e.g., a veterinary method);

1.4 Method 1.3, wherein the animal is a livestock animal, such as a chicken, turkey, geese, duck, pig, cattle, goat, or sheep;

1.5 Method 1.4, wherein method does not result in bioaccumulation of the compound in the livestock animal;

1.6 Method 1.4 or 1.5, wherein method does not result in the accumulation of the compound in livestock animal food products (e.g., meat, such as beef, poultry, pork, or eggs);

1.7 Method 1.6, wherein food products derived from animals treated according to the method comprise less than 5 ppm of the compound, e.g., less than 4 ppm, or less than 3 ppm, or less than 2 ppm, or less than 1 ppm, or less than 0.5 ppm or less than 0.1 ppm;

1.8 Method 1.3, wherein the animal is a non-livestock work animal, such as a horse, donkey, mule, ox, llama, or camel;

1.9 Method 1.3, wherein the animal is a companion animal, such as a dog, cat, rabbit, ferret, rat, or mouse;

1.10 Any of Methods 1.1-1.9, wherein the compound or composition is administered orally to the human or animal, e.g., as a tablet, capsule, liquid solution, oral gel, powder, oral spray, feed additive, edible bait, salt lick, or dietary supplement;

1.11 Any of Methods 1.1-1.9, wherein the compound or composition is administered transdermally to the human or animal, for systemic delivery, e.g., as a liquid solution, gel, or patch;

1.12 Any of Methods 1.1-1.9, wherein the compound or composition is administered topically to the human or animal, such as to the skin, hair, or fur, for local (non-systemic) delivery, e.g., as a liquid solution, spray, gel (e.g., for "spot-on" application), cream, ointment, shampoo, foam, bath, or dip;

1.13 Any of Methods 1.3-1.9, wherein the compound or composition is administered to the animal using a removable collar worn by the animal around the neck;

1.14 Any of Methods 1.1-1.9, wherein the compound or composition is administered to the human or animal as a rapid-acting injection, such as an intravenous, subcutaneous, intramuscular or intraperitoneal injection to provide immediate release of the compound to the animal;

1.15 Any of Methods 1.1-1.9, wherein the compound or composition is administered to the human or animal as a long-acting injection, such as a subcutaneous, intramuscular or intraperitoneal injection using a sustained or delayed release vehicle (e.g., a polymer matrix);

1.16 A method for the treatment, control, suppression, or eradication, of an infection or infestation of an insect (arthropod), such as an adult insect, insect egg, insect larva, insect nymph, and/or insect pupa, comprising applying a Compound of Formula I, or any of 1.1-1.130, or an insecticidal Composition 1 or any of 1.1-1.48, to a plant, plant growth medium, product, or location in need thereof;

1.17 Method 1.16, wherein the compound or composition is applied to plants or media in which plants grow, e.g., agricultural crops, agricultural fields, orchards, vineyards, plantations, or soil for agricultural use;

1.18 Method 1.17, wherein the plant or crop is selected from rice, corn, wheat, sugarcane, potato, rye, oats, barley, millet, soybean, cotton, vegetables (e.g., beans, lettuce, onions, tomatoes, peppers), fruits and nuts (e.g., grapes, apples, citrus, banana, kiwi, avocado, mango, olive, walnut, peanut), tea, coffee, tobacco, and cocoa;

1.19 Method 1.16, wherein the compound or composition is applied to ornamental plants, such as in residential or commercial greenhouses, gardens, or lawns;

1.20 Method 1.16, wherein the compound or composition is applied to residential or commercial locations, e.g., homes, apartment buildings, office buildings, manufacturing facilities, hotels, motels, parks, sporting facilities (e.g., athletic stadiums, golf courses), and other public spaces;

1.21 Method 1.20, wherein the compound or composition is applied to products, e.g., stored food products (e.g., grains, fruits, nuts, spices, tobacco), clothing, bedding, furniture, carpets, rugs, and other household items;

1.22 Any one of Methods 1.16-1.21, wherein the compound or composition is applied as an aerosol spray, e.g., as suspension of solid or liquid particles having a size of less than one micron;

1.23 Any one of Methods 1.16-1.21, wherein the compound or composition is applied as a liquid spray (e.g., a mist of liquid droplets having a droplet size of greater than one micron);

1.24 Any one of Methods 1.16-1.21, wherein the compound or composition is applied by dusting (e.g., a mist of solid particles having a particle size of greater than one micron), or as a bulk liquid, fog, lacquer, paint, or smoke;

1.25 Method 1, or any of 1.1-1.24, wherein the method is intended to kill one or more insects (arthropods), such as adult insects, insect eggs, insect larvae, insect nymphs, and/or insect pupae;

1.26 Method 1.25, wherein the insect (arthropod) is selected from one or more of the following: fleas, lice, ticks, mites, mosquitos, grasshopper, locust, beetles (such as cane beetles, thrips, stink bugs, boxelders, Japanese beetles, emerald ash borer), ants (such as carpenter ants, fire ants), cockroaches, termites, flies, aphids, moths, butterflies, and wasps;

1.27 Method 1.25, wherein the insect (arthropod) is selected from one or more of the following: or example:

- *Acarina* (e.g., tick and mites, such as of the superorders Parasitiformes and Acariformes, and the orders Ixodida, Mesostigmata, Sarcoptiformes, and Trombidiformes), including ticks (e.g., *Ixodes* spp., *Boophilus* spp. e.g., *Boophilus microplus*, *Amblyomma* spp., *Hyalomma* spp., *Rhipicephalus* spp. e.g., *Rhipicephalus appendiculatus*, *Haemaphysalis* spp., *Dermacentor* spp., *Ornithodorus* spp. (e.g., *Ornithodorus moubata*), and mites (e.g., *Dermanyssus* spp. e.g., *Dermanyssus gallinae*, *Ornithonyssus* spp., e.g., *Ornithonyssus sylviarum*, *Sarcoptes* spp. e.g., *Sarcoptes scabiei*, *Psoroptes* spp., *Chorioptes* spp., *Demodex* spp., *Eutrombicula* spp., *Tetranychus* spp., *Panonychus* spp. and *Bryobia* spp. (spider mites), *Eriophyes* spp. (gall mites), *Polyphacotarsonemus* spp., *Varroa* spp., e.g., *Varroa destructor*; Psocodea (lice), including *Anoplura* (e.g., *Pediculus* spp., *Pthirus* spp.), Ischonocera (e.g., *Bovicola* spp., *Damalinia* spp., *Felicola* spp., *Saemundssonia* spp.; *Trichodectes* spp.), and Ambclyera (e.g., *Holomenopon* spp., *Menopon* spp., e.g., *Menopon gallinae*, *Menecanthus* spp., e.g., *Menecanthus stramineus*, *Heterodoxus* spp., e.g., *Heterodoxus spiniger*);
- Chilpoda (centipedes), including Scutigeromorpha (e.g., *Scutigera* spp.);
- Diplopoda (millipedes), including Julida, e.g., *Blaniulus* spp.
- Symphyla (pseudocentipedes), including *Scutigerella* spp., *Symphylella* spp., *Henseniella* spp.;
- Isopoda, including *Oniscus* spp. (woodlice));
- Diptera (flies, including mosquitos), e.g., *Aedes* spp., *Anopheles* spp., *Culex* spp *Musca* spp., *Hypoderma* spp., *Gasterophilus* spp., *Simulium* spp, *Hylemyia* spp. (root flies), *Atherigona* spp. and *Chlorops* spp. (shoot flies), *Phytomyza* spp. (leaf miners), *Ceratitis* spp. (fruit flies);
- Hemiptera (true bugs), e.g., *Triatoma* spp., *Psylla* spp., *Bemisia* spp., *Trialeurodes* spp., *Aphis* spp., *Myzus* spp., *Megoura viciae*, *Phylloxera* spp., *Adelges* spp., *Phorodon humuli* (hop damson aphid), *Aeneolamia* spp. *Nephotettix* spp. (rice leafhoppers), *Empoasca* spp., *Nilaparvata* spp., *Perkinsiella* spp., *Pyrilla* spp., *Aonidiella* spp. (red scales), *Coccus* spp., *Pseucoccus* spp., *Helopeltis* spp. (mosquito bugs), *Lygus* spp., *Dysdercus* spp., *Oxycarenus* spp, and *Nezara* spp.;
- Phthiraptera (louses) (e.g., *Damalinia* spp., *Linognathus* spp.);
- Siphonaptera (fleas), e.g., *Ctenocephalides* spp., *Tunga* spp., *Ceratophyllus* spp.;
- Blattodea (cockroaches), e.g., *Periplaneta* spp., *Blatella* spp.;
- Hymenoptera (sawflies, wasps, ants), e.g., *Athalia* spp., *Cephus* spp. (saw flies), *Atta* spp. (leaf cutting ants), *Vespula* spp., *Dolichovespula* spp., *Vespa* spp., *Linepithema* spp., *Solenopsis* spp., *Anoplolepis* spp., *Camponotus* spp., *Formica* spp., *Myrmica* spp., and *Monomorium* spp., e.g., *Monomorium pharaonis*;
- Coleoptera (beetles), including *Ephestia* spp. (flour moths), *Anthrenus* spp. (carpet beetles), *Tribolium* spp. (flour beetles), *Sitophilus* spp. (grain weevils), e.g., *Hypothenemus hampei* (coffee berry borer), *Hylesinus* spp. (bark beetles), *Anthonomus grandis* (cotton boll weevil), *Acalymma* spp. (cucumber beetles), *Lema* spp., *Psylliodes* spp., *Leptinotarsa decemlineata* (Colorado potato beetle), *Diabrotica* spp. (corn rootworms), *Gonocephalum* spp. (false wire worms), *Agriotes* spp. (wireworms), *Dermolepida* and *Heteronychus* spp. (white grubs), *Phaedon cochleariae* (mustard beetle), *Lissorhoptrus oryzophilus* (rice water weevil), *Melioethes* spp. (pollen beetles), *Ceutorhynchus* spp., *Rhynchophorus* and *Cosmopolites* spp. (root weevils);
- Lepidoptera (butterflies and moths, including their caterpillars and worms), e.g., *Heliothis* spp. such as *Heliothis virescens* (tobacco budworm), *Heliothis armioera* and *Heliothis zea*, *Spodoptera* spp. such as *S. exempta*, *S. littoralis* (Egyptian cotton worm), *S. eridania* (southern army worm), *Mamestra configurata* (bertha army worm); *Earias* spp. e.g., *E. insulana* (Egyptian bollworm), *Pectinophora* spp. e.g., *Pectinophora gossypiella* (pink bollworm), *Ostrinia* spp. such as *O. nubilalis* (European cornborer), *Trichoplusia ni* (cabbage looper), *Pieris* spp. (cabbage worms), *Laphygma* spp. (army worms), *Agrotis* and *Amathes* spp. (cutworms), *Wiseana* spp. (porina moth), *Chilo* spp. (rice stem borer), *Tryporyza* spp. and *Diatraea* spp. (sugar cane borers and rice borers), *Sparganothis pilleriana* (grape berry moth), *Cydia pomonella* (codling moth), *Archips* spp. (fruit tree *tortrix* moths), and *Plutella* spp., e.g., *Plutella xylostella* (diamond back moth);
- Thysanoptera (thrips), such as *Anaphothrips* spp., *Megalurothrips* spp., *Scirtothrips* spp., *Sorgothrips* spp., *Frankiniella* spp., and *Thrips* spp., e.g., *Thrips tabaci*;
- Orthoptera such as *Locusta* and *Schistocerca* spp. (locusts) and crickets e.g., *Gryllus* spp. and *Acheta* spp.;
- Collembola (springtails), e.g., *Sminthurus* spp. and *Onychiurus* spp.;
- Isoptera and Neoisoptera (termites), e.g., *Odontotermes* spp., *Reticulitermes* spp., *Heterotermes* spp., *Coptotermes* spp.;
- *Dermaptera* (earwigs), e.g., *Forficula* spp.;

1.28 Method 1.25, wherein the insect is a mite of the superorder Parasitiformes, e.g., a mite of the order Mesostigmata, such as a mite of the family Dermanyssidae or Macronyssidae, such as a mite of the genus *Dermanyssus* (e.g., *Dermanyssus gallinae*) or *Ornithonyssus* (e.g., *Ornithonyssus sylviarum*), in particular the poultry mite or red mite, *Dermanyssa gallinae*;

1.29 Method 1, or any of 1.1-1.28, wherein the method further comprises the co-administration of one or more other insecticidal agents (e.g., concurrently, consecutively, or alternately);

1.30 Method 1.29, wherein the one or more other insecticidal agents are selected from: phenylpyrazoles, pyrethroids, neonicotinoids, organochlorines, organophosphates, butenolides, carbamates, and diamides (Ryanoids);

1.31 Method 1.29, wherein the one or more other insecticidal agents are selected from fipronil, acetoprole, ethiprole, flufiprole, pyraclofos, pyrafluprole, pyriprole, pyrolan, and vanilliprole, allethrin, bifenthrin, cyfluthrin, cypermethrin, cyphenothrin, deltamethrin, dimefluthrin, esfenvalerate, etofenprox, fenpropathrin, fenvalerate, flucythrinate, flumethrin, imiprothrin, cyhalothrin (e.g., lambda cyhalothrin), metofluthrin, permethrin, phenothrin, prallethrin, resmethrin, silafluofen, fluvalinate (e.g., tau fluvalinate), tefluthrin, tetramethrin, tralomethrin, transfluthrin, acetamiprid, clothiandin, dinotefuran, imidacloprid, nitenpyram, nithiazine, thiacloprid, thiamethoxam, aldrin, chlordane, dieldrin, endosulfan, endrin, heptachlor, azamethiphos, azinphos methyl, chlorpyrifos, diazinon, dichlorvos, fenitrothion, malathion, parathion, parathion methyl, phosmet, terbufos, tetrachlorvinphos, flupyradifurone, aldicarb, bendiocarb, carbofuran, carbaryl, ethienocarb, fenobucarb, oxamyl, methomyl, and chlorantraniliprole;

1.32 Method 1, or any of 1.1-1.31, wherein the compound or composition is administered to the animal or human patient four times per day, three times per day, two times per day, once per day, once every other day, once every three days, once every four days once every five days, once every six days, once per week, once every two weeks, once every three weeks, once per month, once every two months, once every three months, or once every six months, until the patient no longer is need of the compound or composition;

1.33 Method 1, or any of 1.1-1.31, wherein the compound or composition is applied to the location or product four times per day, three times per day, two times per day, once per day, once every other day, once every three days, once every four days once every five days, once every six days, once per week, once every two weeks, once every three weeks, once per month, once every two months, once every three months, or once every six months, until there is no longer a need for application of the compound or composition;

1.34 Method 1, or any of 1.1-1.33 wherein the compound applied is the Compound of Formula I of the following formula:

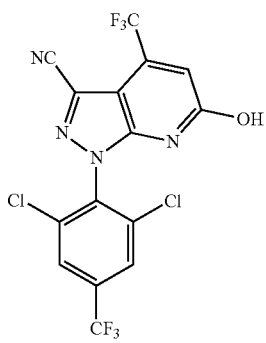 [SMILES: N#Cc1nn(-c2c(Cl)cc(C(F)(F)F)cc2Cl)c2nc(O)cc(C(F)(F)F)c12]

in free or salt form;

1.35 Method 1, or any of 1.1-1.34, wherein the compound is applied as an aqueous solution, optionally comprising an organic co-solvent (e.g., methanol, ethanol, isopropanol, methoxymethanol, ethoxyethanol, 2-butoxyethanol);

1.36 Method 1.35, wherein the solution comprises 2-butoxyethanol, ethanol and water;

1.37 Method 1.36, wherein the solution comprises 2-butoxyethanol, ethanol, and water in a 7:2:1 v/v ratio, e.g., the composition comprises the Compound of Formula I dissolved, dispersed, or suspended in the solution comprising 2-butoxyethanol, ethanol, and water in a 7:2:1 v/v ratio;

1.38 Method 1.34, wherein the solution comprises ethanol and water;

1.39 Method 1.38, wherein the solution comprises ethanol and water in an about 75:25 to 99:1 v/v ratio, e.g., 75:25 to 95:5, or 75:25 to 90:10, or 75:25 to 85:15, or 75:25 to 80:20, or 80:20 to 99:1, or 80:20 to 95:5, or 80:20 to 90:10, or 80:20 to 85:15, or 85.15 to 99:1, or 85:15 to 95:5, or 85:15 to 90:10, or 90:10 to 99:1, or 90:10 to 95:5, or 95:5 to 99:1, or about 80:20, or about 85:15, or about 90:10, or about 95:5, or about 99:1, v/v;

1.49 Method 1, or any of 1.1-1.34, wherein the compound is applied as an aqueous suspension, optionally comprising an organic co-solvent (e.g., methanol, ethanol, isopropanol, methoxymethanol, ethoxyethanol, 2-butoxyethanol);

1.50 Method 1.49, wherein the suspension comprises 2-butoxyethanol, ethanol and water;

1.51 Method 1.50, wherein the suspension comprises 2-butoxyethanol, ethanol, and water in a 7:2:1 v/v ratio, e.g., the suspension comprises the Compound of Formula I suspended in the solution comprising 2-butoxyethanol, ethanol, and water in a 7:2:1 v/v ratio;

1.52 Method 1.49, wherein the suspension comprises ethanol and water;

1.53 Method 1.52, wherein the suspension comprises ethanol and water in an about 1:99 to 75:25 v/v ratio, e.g., 10:90 to 75:25, or 20:80 to 75:25, or 30:70 to 75:25, or 40:60 to 75:35, or 50:50 to 75:25, or 55:45 to 75:25, or 60:40 to 75:25, or 65:35 to 75:25, or 70:30 to 75:25, v/v;

1.54 Method 1, or any of 1.1-1.40, wherein the compound is applied or administered as a composition, and the composition comprises the Compound of Formula I in an amount of 0.1 to 1.0%, e.g., 0.1 to 0.5%, or 0.2 to 0.3%, or about 0.25%, w/v;

1.55 Method 1, or any of 1.1-1.54, wherein the compound is applied or administered as a composition, and the composition is prepared from a concentrate, which comprises the Compound of Formula I in an amount of 1 to 20%, e.g., 1 to 15%, or 1 to 10%, or 1 to 5% w/v, and wherein the concentrate is diluted with water and/or an organic co-solvent (e.g., methanol, ethanol, isopropanol, methoxymethanol, ethoxyethanol, 2-butoxyethanol), prior to use, e.g., to provide a final concentration of the Compound of Formula I of 0.1 to 1.0%, e.g., 0.1 to 0.5%, or 0.2 to 0.3%, or about 0.25%, w/v, in the composition applied or administered;

1.56 Method 1, or any of 1.1-1.55, wherein the compound or composition is formulated for delivery by spray (e.g., liquid spray or aerosol spray);

1.57 Method 1, or any of 1.1-1.56, wherein the method is carried out to treat, control, suppress, or eradicate, an infection or infestation of an insect (arthropod), such as an adult insect, insect egg, insect larva, insect nymph, and/or insect pupa, wherein the insect is the poultry mite or red mite, *Dermanyssus gallinae*;

1.58 Method 1.57, wherein the mite is infecting chickens or infesting chicken coops, chicken pens, chicken cages, other chicken enclosures, chicken farms, or chicken feed;

1.59 Method 1.57, wherein the method is carried out by administering the composition to chickens or applying the composition to chicken coops, chicken pens, chicken cages, other chicken enclosures, chicken farms, or chicken feed;

1.60 Method 1, or any of 1.1-1.59, wherein the method is carried out to treat, control, suppress, or eradicate, an infection or infestation of an insect (arthropod), such as an adult insect, insect egg, insect larva, insect nymph, and/or insect pupa, wherein the insect is selected from one or more of fleas, ticks, mites, lice, fire ants, termites, beetles, cockroaches, mole crickets, thrips, rootworms, and weevils.

In a fourth aspect, the present disclosure provides a Compound of Formula IL or any of 1.1-1.130, or a pharmaceutical or insecticidal Composition 1, or any of 1.1-1.48, for use in the treatment, control, suppression, or eradication, of an infection or infestation of an insect (arthropod), such as an adult insect, insect egg, insect larva, insect nymph, and/or insect pupa, for example, according to Method 1 or any of 1.1-1.60.

In a fourth aspect, the present disclosure provides the use of a Compound of Formula I, or any of 1.1-1.130, or a pharmaceutical or insecticidal Composition 1, or any of 1.1-1.48, for the treatment, control, suppression, or eradication, of an infection or infestation of an insect (arthropod), such as an adult insect, insect egg, insect larva, insect nymph, and/or insect pupa, for example, according to Method 1 or any of 1.1-1.60.

The compounds of Formula I, and the Compositions comprising said compounds, are expected to be of broad-spectrum insecticidal activity. The compounds and compositions are generally effective to kill a wide variety of arthropods, including, but not limited to, Chelicerates, including arachnids, such as ticks, mites, and spiders, Myriapods, such as millipedes, centipedes, and symphylans, and Pancrustaceans including woodlice (Class Malacostraca, Order Isopoda), insects (Class Insecta) and springtails (Class Collembola). Thus, it is understood that the term "insect" as used herein is not limited to arthropods of the Class Insecta (i.e., true insects), but rather, includes a variety of arthropods that are not phylogenetically classified as insects. Likewise, the terms "insecticide" and "insecticidal" as used herein are indicative of the property of a compound or composition being effective to kill true insects, as well as other arthropods, including Chelicerates such as arachnids (ticks, mites, spiders), Myriapods and non-insect Pancrustaceans such as woodlice and springtails.

In particularly preferred embodiments of the present disclosure, the compounds and compositions disclosed herein are useful as, and used for, the control of ticks and mites, e.g., arthropods of the superorders Parasitiformes (mites and ticks) and Acariformes (mites), which belong to the Class Arachnida, of the subphylum *Chelicerata* In particular, within the superorder Parasitiformes, this includes arthropods of the Orders Ixodida (ticks), and Mesostigmata (mites), and within the superorder Acariformes, this includes arthropods (mites) of the Orders Sarcoptiformes and Trombidiformes.

Compositions according to the present disclosure may generally be in the form of solids, liquids, or semisolids, including powders, granules, aggregates, blocks, solutions, suspensions, dispersions, emulsions, mists, aerosols, fogs, foams, gels, creams, pastes, ointments, and gums. Liquid compositions include water miscible concentrates, emulsifiable concentrates, flowable suspensions, wettable or soluble powders, which may be used to treat substrates or sites infested or liable to infestation by insects (arthropods), including premises, outdoor or indoor storage or processing areas, containers or equipment and standing or running water.

Compounds and compositions according to the present disclosure may generally be administered to animals by incorporation in feed or suitable orally-ingestible pharmaceutical formulations, edible baits, salt licks, dietary supplements, pour-on formulations, sprays, baths, dips, showers, jets, dusts, greases, shampoos, creams, or wax-smears.

Compounds and compositions according to the present disclosure may generally be applied to the environment, either in general or to specific locations where pests may lurk, including stored products, timber, household goods, and domestic and industrial premises, as sprays, fogs, dusts, smokes, wax-smears, lacquers, granules and baits, as trickle feeds to waterways, wells, reservoirs and other running or standing water.

Compounds and compositions according to the present disclosure may generally be applied to growing crops as foliar sprays, dusts, granules, fogs and foams, or as suspensions of finely divided and encapsulated compounds; as soil and root treatments by liquid drenches, dusts, granules, smokes and foams, and as seed dressings by liquid slurries and dusts.

Solid compositions, such as dusts, granules or wettable powders, are generally prepared by impregnating solid diluents with solutions of the compound of Formula I in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g., gelatin, synthetic resins and polyamides. The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrous sorbitols which have been rendered soluble by etherification of the free hydroxy groups by condensation with ethylene oxide, or mixtures of these types of agents. Wettable powders may be treated with water immediately before use to give suspensions ready for application.

Liquid compositions may incorporate natural or synthetic polymers, wetting, dispersing or emulsifying agents. Liquid compositions may be prepared using aqueous, organic or aqueous-organic diluents, for example acetophenone, isophorone, toluene, xylene, mineral, animal or vegetable oils, and water-soluble polymers (and mixtures of these diluents), which may contain wetting, dispersing or emulsifying agents of the ionic or non-ionic types or mixtures thereof.

Compositions according to the present disclosure may also contain synergists (e.g., piperonyl butoxide or sesamex), stabilizing substances, other insecticides, acaricides, plant nematocides, anthelmintics or anticoccidials, fungicides (agricultural or veterinary as appropriate e.g., benomyl, iprodione), bactericides, arthropod or vertebrate attractants or repellents or pheromones, deodorants, flavoring agents, dyes, taste masking agents, and auxiliary therapeutic agents, e.g., trace elements. These may be designed to improve potency, persistence, safety, uptake where desired, spectrum of pests controlled or to enable the composition to perform other useful functions in the same animal or area treated.

The compositions of the present disclosure may typically comprise from 0.00001% to 95% by weight, or more particularly from 0.0005% to 50% by weight, of the Compound or Compounds of Formula I and/or of total active ingredients (Compounds of Formula I and any additional insecticidal agents, synergists, trace elements or stabilizers). The actual compositions employed and their rate of application will be selected to achieve the desired effect(s) by the farmer, livestock producer, medical or veterinary practitioner, pest control operator, or other person skilled in the art.

Solid and liquid compositions for application topically to animals, timber, stored products or household goods usually contain from 0.00005% to 90%, more particularly from 0.001% to 10%, by weight of one or more Compounds of Formula I For administration to animals orally or parenterally, including percutaneously solid and liquid compositions normally contain from 0.1% to 90% by weight of one or more Compound of Formula I. Medicated feedstuffs normally contain from 0.001% to 3% by weight of one or more Compounds of Formula I. Concentrates and supplements for mixing with feedstuffs normally contain from 5% to 90%, and preferably from 5% to 50%, by weight of one or more Compound of Formula I. Mineral salt licks normally contain from 0.1% to 10% by weight of one or more Compound of Formula I.

Dusts and liquid compositions for application to livestock, persons, goods, premises or outdoor areas may contain 0.0001% to 15%, and more especially 0.005% to 2.0%, by weight of one or more Compound of Formula I. Suitable concentrations in treated waters are between 0.0001 ppm and 20 ppm, and more especially 0.001 ppm to 5.0 ppm of one or more Compound of Formula I and may also be used therapeutically in fish farming with appropriate exposure times. Edible baits may contain from 0.01% to 5% and preferably 0.01% to 1.0%, by weight of one or more Compound of Formula I.

When administered to vertebrates parenterally, orally or by percutaneous or other means, the dosage of Compound of Formula I will depend upon the species, age and health of the vertebrate and upon the nature and degree of its actual or potential infestation by the pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the claims are used herein to refer to one or to more than one (i.e., to at least one) of the grammatical object of the article unless the context clearly indicates otherwise. By way of example, "an element" means one element or more than one element.

The phrase "and/or" as used herein and in the claims should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive. i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of".

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the term "about" is normally used to encompass values within the standard deviation or standard error. In some embodiments, "about" may be interpreted as +/−10% of the stated value.

In the claims, as well as in the specification, all transitional phrases such as "comprising," "including," "carrying," "having," "containing," "involving," "holding," "composed of," and the like are to be understood to be open-ended, i.e., to mean "including without limitation." Only the transitional phrases "consisting of" and "consisting essentially of" shall be closed or semi-closed transitional phrases, respectively.

It should also be understood, that although various compounds, compositions, and methods are described in "open" terms of "comprising," "including," or "having" various components or steps (interpreted as meaning "including without limitation"), the compounds, compositions, methods, and devices can also "consist essentially of" or "consist of" the various components and steps, and such terminology should be interpreted as defining essentially closed-member groups. This paragraph is not meant in any way to limit the meaning of "comprising," "having," or "including" (and other verb forms thereof) which are to be interpreted as open-ended phrases meaning "including without limitation" consistent with patent law and custom. The intent of this paragraph is merely to indicate that the closed-member groups defined by the "consisting of" or "consisting essentially of" language are lesser included groups within the open-ended descriptions and to provide support for claims employing the "consisting of" or "consisting essentially of" language.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In some embodiments, one or more of the present compounds described herein, are co-administered in combination with at least one additional bioactive agent, such as another anticancer agent. In some embodiments, the co-administration of compounds results in synergistic activity and/or therapy, including anticancer activity.

The term "effective" can mean, but is in no way limited to, that amount/dose of the active pharmaceutical or insecticidal ingredient, which, when used in the context of its intended use, effectuates or is sufficient to provide the intended outcome, e.g., the treatment, control, suppression, or eradication, of an infection or infestation of an insect (arthropod), such as an adult insect, insect egg, insect larva, insect nymph, and/or insect pupa.

The effective amount depends on the type and severity of disease or infestation, the composition used, the route of administration or application, the type of animal or location being treated, concurrent treatment with or application of other insecticidal agents, and other factors which those skilled in the medical arts will recognize.

The term "pharmaceutically acceptable" can mean, but is in no way limited to, entities and compositions that do not produce an adverse, allergic or other untoward reaction when administered to a patient or subject.

The term "pharmaceutically acceptable carrier" can mean, but is in no way limited to, any and all solvents, excipients, coatings, and the like, compatible with pharmaceutical administration to a patient or subject. Such ingredients include diluents, binders, lubricants, dispersants, surfactants, tonicity agents, stabilizer, solubilizing agents, gelling agents, complexing agents, antioxidants, buffers, flavors, colors, and coatings. Suitable solvents and excipients include, but are not limited to water, ethanol, dimethylsulfoxide, polyethylene glycol, polypropylene glycol, poloxamers (ethylene oxide/propylene oxide block copolymers), mannitol, sorbitol, glycerin, carboxymethyl cellulose, sodium carboxymethyl cellulose, hydroxypropyl methyl cellulose, hydroxyethyl cellulose, hydroxypropyl cellulose, methylcellulose, ethylcellulose, cellulose acetate, polyvinyl alcohol, polyvinyl acetate, polyvinyl acetate-polyvinyl alcohol copolymer, polyvinylpyrrolidone, polyacrylate, polymethyl acrylate, polymethyl methacrylate, xanthan gum, gum arabic, guar gum, karaya gum, agar, alginic acid, sodium alginate, carrageenan, gum tragacanth, locust bean gum, glucan, gellan gum, sodium lauryl sulfate, sodium laureth sulfate, cocamidopropyl betaine, polyoxyethylene sorbitan esters (e.g., polysorbate 20, polysorbate 40, polysorbate 60, polysorbate 65, polysorbate 80), dimethicone, diethyl phthalate, stearic acid, cetyl alcohol, magnesium stearate, magnesium aluminum silicate, silicon dioxide, starch (e.g., pregelatinized starch), sodium starch glycolate, talc, triethyl citrate, glyceryl triacetate, dextrose, maltose, lactose, trehalose, calcium carbonate, dicalcium phosphate, sodium chloride, potassium chloride, sodium hydroxide, sodium carbonate, sodium bicarbonate, sodium citrate, sodium phosphate, sodium acetate, hydrochloric acid, acetic acid, citric acid, tartaric acid, phosphoric acid, propyl gallate, sodium metabisulfite, butylated hydroxyanisole, butylated hydroxytoluene, and alpha-tocopherol.

The term "insecticidally acceptable" can mean, but is in no way limited to, entities and compositions that do not produce an unacceptable adverse outcome when applied to a product or location, such as an unacceptably adverse hazardous or environmental outcome.

The term "insecticidally acceptable carrier" can mean, but is in no way limited to, any and all solvents, excipients, coatings, and the like, compatible with insecticidal administration to a product or location. Suitable carriers and excipients include all of the pharmaceutically acceptable and suitable carriers and excipients listed in the preceding paragraphs, and in addition: methanol, isopropanol, 2-butoxyethanol, ethylene glycol, hexylene glycol, 1,3-propanediol, 1,2-propanediol, diethylene glycol, diethanolamine, aluminum oxide, aluminum oxide silicate, trisodium sulfosuccinate, cobalt propionate, 2-ethylhexyl octadecenoate, ethylene oxide/oleic acid monoethanolamide, butyl 2-propenoate polymers and copolymers, sodium dodecylnaphthalene sulfonate, decamethyl cyclopentasiloxane, cyclodextrins, sodium silicate, ammonium dodecanoate, sodium benzoate, boric acid, sodium borate, and mica.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral (enteral) administration or parenteral (e.g., intravenous injection). Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

The terms "patient" or "subject" may describe a cell, tissue, or animal, preferably a mammal, e.g., a human, livestock animal, or companion animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc.

The term "compound," as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, atropisomers, as well as salts, hydrates, solvates, polymorphs, and derivatives thereof where applicable, in context. Such isomers include, in the context of double and triple bonds and ring systems, both cis- and trans-isomers. Within its use in context, the term, "compound" generally refers to a single compound, but also may include other compounds such as stereoisomers, regioisomers and/or optical isomers (including racemic mixtures) as well as specific enantiomers or enantiomerically enriched mixtures of disclosed compounds. The term also refers to any specific chemical compound in which one or more atoms have been replaced with one or more different isotopes of the same element (e.g., hydrogen replaced by deuterium). It is noted that in describing the present compounds, numerous substituents and variables associated with same, among others, are described.

"Tautomers" refer to compounds that are interchangeable forms of a particular compound structure, and that vary in the displacement of hydrogen atoms and electrons. Thus, two structures may be in equilibrium through the movement of pi-electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base. Tautomeric forms may be relevant to the attainment of the optimal chemical reactivity and biological activity of a compound of interest.

It is understood by those of ordinary skill that molecules which are described herein are stable compounds as generally described hereunder. When the bond is shown, both a double bond and single bond are represented or understood within the context of the compound shown and well-known rules for valence interactions.

As used herein, "derivatives" can mean compositions formed from the native compounds either directly, by modification, or by partial substitution. As used herein, "analogs" can mean compositions that have a structure similar to, but not identical to, the native compound.

Amino refers to the group —NH$_2$; hydroxy refers to the group "—OH"; cyano refers to the —CN group; nitro refers to the group —NO$_2$. It is understood that the groups amino and hydroxy are both optionally substitutable, such as, by acyl groups and the like. However, because mono- and di-alkyl amino groups and alkoxy groups (i.e., alkyloxy groups) are separately enumerated herein, alkyl substitution of amino and hydroxy groups is not intended in the term "optionally substituted" as applied to these groups.

"Halo" or "halogen" refers to fluoro (F), chloro (Cl), bromo (Br) or iodo (I).

"Alkyl" as used herein means an acyclic linear or branched fully saturated hydrocarbon moiety, preferably having one to six carbon atoms, or in some embodiments, one to four carbon atoms, or one to three carbon atoms, which, unless indicated otherwise, may be optionally substituted, as defined herein. Exemplary alkyl groups include, but are not limited to, methyl, ethyl, propyl, isopropyl, n-butyl, sec-butyl, isobutyl, t-butyl, n-pentyl, isopentyl, neopentyl, n-hexyl, n-heptyl, n-octyl, n-nonyl, n-decyl, or any other acyclic hydrocarbon group having the general formula —C$_n$H$_{2n+1}$.

"Alkenyl" as used herein means an acyclic linear or branched unsaturated hydrocarbon moiety having at least one carbon-carbon double bond, preferably having two to six carbon atoms, or in some embodiments, two to four carbon atoms, or two to three carbon atoms, which, unless indicated otherwise, may be optionally substituted, as defined herein. Preferably, said group is mono-unsaturated (having a single carbon-carbon double bond). Examples of alkenyl groups include, but are not limited to, vinyl and allyl, or any other hydrocarbon acyclic group having the general formula —C$_n$H$_{2n-1}$.

"Alkynyl" as used herein means an acyclic linear or branched unsaturated hydrocarbon moiety having at least one carbon-carbon triple bond, preferably having two to six carbon atoms, or in some embodiments, two to four carbon atoms, or two to three carbon atoms, which, unless indicated otherwise, may be optionally substituted, as defined herein. Preferably, said group is mono-unsaturated (having a single carbon-carbon triple bond). Examples of alkynyl groups include, but are not limited to, ethynyl and propargyl, or any other hydrocarbon acyclic group having the general formula —C$_n$H$_{2n-3}$. As used herein, a hydrocarbon radical having both a double bond and a triple bond is considered an alkynyl radicals.

"Alkylene" as used herein means a —(CH$_2$)$_n$— group, e.g., wherein n is an integer generally from 1-10, such as 1-6, which may be optionally substituted, as defined herein. When substituted, the alkylene group preferably is substituted on one or more of the methylene (CH$_2$) groups with a C$_1$-C$_6$ alkyl group (including a cyclopropyl group or a t-butyl group), more preferably a methyl group, but may also be substituted with one or more halo groups, preferably from 1 to 3 halo groups, or one or two hydroxyl groups, amino groups, alkoxy groups, cycloalkyl groups, or cycloalkoxy groups, as defined herein.

"C$_{1-6}$haloalkyl" as used herein means an alkyl group, as defined above, having from one to six carbon atoms, and substituted by at least on halogen atom (e.g., F, C, Br, or I), and up to the maximum number of halogen atoms permitted by the valence of the carbon atoms of the alkyl group, which may be further optionally substituted, as defined herein. The group may be substituted by multiple atoms of the same halogen, or different halogens. C$_{1-6}$haloalkyl includes, for example, fluoromethyl, difluoromethyl, trifluoromethyl, 2-fluoroethyl, 2,2-difluoroethyl, 2,2,2-trifluoroethyl.

"Alkoxy" as used herein means a group of the structure —O-(alkyl), which may be optionally substituted, as defined herein. Thus, for example, a C$_{1-6}$alkoxy group is a group having the structure —O—($C_{1-6}$alkyl). An alkoxy radical attaches to the structure to which it is appended by its oxygen atom.

"Cycloalkyl" as used herein means a nonaromatic saturated or unsaturated free radical forming at least one ring, having, for example, 3 to 10 carbon atoms and a corresponding number of hydrogen atoms, which may be optionally substituted, as defined herein. The term "cycloalkyl" therefore includes carbocyclic rings having one or more double or triple bonds. Cycloalkyl groups can be monocyclic or polycyclic. Individual rings of such polycyclic cycloalkyl groups can have different connectivities, e.g., fused, bridged, spiro, etc., in addition to covalent bond substitution. Exemplary cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl, adamantyl, substituted with cyclobutyl, cyclobutyl substituted with cyclopentyl, cyclohexyl substituted with cyclopropyl, etc. Of course, other cycloalkyl groups will be readily apparent to those of skill in the art given the benefit of the present disclosure.

"Cycloalkoxy" as used herein means a group of the structure —O-(cycloalkyl), which May be optionally substituted, as defined herein. Thus, for example, a $C_{3-6}$cycloalkoxy group is a group having the structure —O—($C_{3-6}$cycloalkyl). A cycloalkoxy radical attaches to the structure to which it is appended by its oxygen atom.

"Halocycloalkyl" as used herein means a cycloalkyl group, as defined above, substituted by at least on halogen atom (e.g., F, Cl, Br, or I), and up to the maximum number of halogen atoms permitted by the valence of the carbon atoms of the alkyl group, which may be further optionally substituted, as defined herein. The group may be substituted by multiple atoms of the same halogen, or different halogens. Halocycloalkyl groups include, for example, 1-fluorocyclopropyl, 2-fluorocyclopropyl, 2,2-difluorocyclopropyl, 2,2-difluorocyclobutyl, 3,3-difluorocyclopentyl, and the like.

"Heterocycloalkyl" as used herein means any cyclic nonaromatic ring system comprising at least one heteroatom (e.g., N, S, or O) ring atom. This includes 3- to 13-membered monocyclic and fused bicyclic ring systems, and any larger multi-Ming fused ring systems, as long such ring systems do not comprise any aromatic carbocyclic or aromatic heterocyclic ring. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom. Of course, other heterocycloalkyl groups will be readily apparent to those of skill in the art given the benefit of the present disclosure.

"Aryl" as used herein means any carbocyclic aromatic ring system, i.e., any aromatic ring system comprising only carbon atoms as ring atoms. This includes 6-membered monocyclic aryl ring systems and 9-membered or 10-membered fused bicyclic aryl ring systems, and larger fused ring systems, as long such ring systems comprise at least one 6-membered aromatic carbocyclic ring (i.e., a benzene ring) within the fused ring system, and as long as no ring-atoms are heteroatoms. Aryl includes, but is not limited to, phenyl, naphthyl, phenanthryl, and anthracenyl.

"Heteroaryl" as used herein means any cyclic heteroaromatic ring system, i.e., any aromatic ring system comprising at least one heteroatom (e.g., N, S, or O) ring atom. This includes 5-membered and 6-membered monocyclic heteroaryl ring systems and 9-membered or 10-membered fused bicyclic heteroaryl ring systems, and larger fused ring systems, as long such ring systems comprise at least one aromatic carbocyclic or aromatic heterocyclic ring within the fused ring system and at least one heteroatom (e.g., N, S or O) ring-atom within the fused ring system (either in an aromatic ring or non-aromatic ring). Heteroaryl therefore includes, but is not limited to, bicyclic fused ring systems selected from aromatic-heteroaromatic, aromatic-heterocyclic, heteroaromatic-carbocyclic, heterocyclic-aromatic, and heteroaromatic-heteroaromatic, as well as larger fused ring systems comprising some combination of benzene, cycloalkane, heterocycloalkane and heteroaromatic rings. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, pyridonyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5,6,7,8-tetrahydro-quinolin-3-yl, benzoxazolyl, benzofuranyl, isobenzofuranyl, benzothiazolyl, benzisothiazolyl, benzisoxazolyl, benzimidazolyl, benzothiadiazolyl, thionaphthenyl, isothianaphthenyl, benzofuranyl, isobenzofuranyl, isoindolyl, indolyl, indolizinyl, indazolyl, isoquinolinyl, quinolinyl, phthalazinyl, quinoxalinyl, quinazolinyl, naphthyridyl, phenanthridinyl, acridinyl, carbazolyl, carbazolinyl, permidinyl, phenanthrolinyl, phenacenyl, pyrrolopyrimidinyl, pyrrolopyridinyl, pyridopyrimidinyl, theinopyrimidinyl, furopyrimidinyl, furopyridyl, furopyrrolyl, pyrazoloxazolyl, thienofuranyl, imidazothiazolyl, imidazopyridyl, imidazotriazyl, imidazopyrimidinyl, pyrazinopyridazinyl, phenothiazinyl, furazanyl, phenoxazinyl, pyrazo benzoxazinyl, azaindolizinyl, dihydroquinolinyl, dihydroisoquinolinyl, tetrahydroquinolinyl, tetrahydroisoquinolinyl, and pyridoxazinyl. It is understood that for heteroaryl systems in which the both ring carbon atoms and ring heteroatoms have open valencies, bonds can be formed to either such atom types (e.g. C-linked or N-linked). For example, where a pyrazolyl moiety is a substituent, and further substituted with other groups, either the core structure tow which the pyrazolyl is attached, and any one or more other substituents attached to the pyrazolyl, may be attached through a pyrazole ring nitrogen atom (N-linked) or a pyrazole ring carbon atom (C-inked).

As used herein, the term "unsubstituted" means that the indicated structure or group is further substituted only with hydrogen atoms.

As used herein, the term "substituted" or "optionally substituted" means that one or more hydrogen atoms of a group or radical is independently (i.e., where more than a single substitution occurs, each substituent is independent of another substituent) replaced by one or more non-hydrogen substituents, up to the maximum permissible number of substituents for the chemical structure, substructure, group or radical, for example, up to five substituents, preferably up to three substituents, often 1 or 2 substituents on a moiety. Substituents may themselves be further substituted. Optional substituents, unless otherwise indicated, include hydroxy (—OH), thiol (—SH), carboxy (—COOH), cyano (—CN), nitro (—NO$_2$), halo (preferably, F or Cl), $C_1$-$C_{20}$alkyl (e.g., $C_1$-$C_{10}$alkyl, $C_1$-$C_6$alkyl), $C_2$-$C_{20}$alkenyl (e.g., $C_2$-$C_{10}$alkenyl, $C_2$-$C_6$alkenyl), $C_2$-$C_{20}$alkynyl (e.g., $C_2$-$C_{10}$alkynyl, $C_2$-$C_6$alkynyl), aryl (e.g., phenyl, naphthyl), heteroaryl (e.g., 5- to 10-membered ring heteroaryls, such as azoles, diazoles, triazoles, pyridine, diazines, triazines, and benzo-fused derivatives thereof), 5-10 membered heterocycloalkyl (containing at least one heteroatom N, S, or O), $C_1$-$C_{20}$alkoxy (e.g., $C_1$-$C_{20}$alkoxy, $C_1$-$C_6$alkoxy), $C_3$-$C_{20}$cycloalkyl (e.g., $C_3$-$C_{10}$cycloalkyl, $C_3$-$C_6$cycloalkyl), $C_3$-$C_{20}$cycloalkoxy (e.g., $C_3$-$C_{10}$cycloalkoxy, $C_3$-$C_6$cycloalkoxy), aryloxy (e.g., phenoxy), thioether (thio$C_1$-$C_6$alkyl or aryl), keto, acyl (preferably, $C_1$-$C_6$ acyl), ester or thioester (preferably, $C_1$-$C_6$ alkyl or aryl; including alkylene ester, such that attachment is on the alkylene group, rather than at the ester function which is preferably substituted with a $C_1$-$C_6$ alkyl or aryl group), amine (including amino (—NH$_2$), mono-$C_1$-$C_6$alkylamino, di-$C_1$-$C_6$alkylamino, five- or six-membered N-containing heterocycloalkyl), carbamate or urethane (such as optionally substituted N($C_0$-$C_6$ alkyl)C(O)(O$C_1$-$C_6$ alkyl) group), hydrazine or hydrazide, amido (N—C(O), preferably substituted with one or two $C_1$-$C_6$ alkyl groups; including a carboxamido which is optionally substituted with one or two $C_1$-$C_6$ alkyl groups), sulfone (SO$_2$), sulfoxide (S(O)), sulfonamide, alkanol (preferably, $C_1$-$C_6$ alkyl or aryl, such as (CH$_2$)$_n$OH), or alkanoic acid (preferably, $C_1$-$C_6$ alkyl or aryl, such as (CH$_2$)$_n$COOH), wherein n is an integer from 1-10, e.g., 1-6. Substituents according to the present invention may also include SiR$_1$R$_2$R$_3$ groups wherein each of R$_1$ and R$_2$ is as otherwise described herein, and R$_3$ is H or a $C_1$-$C_6$ alkyl group, preferably R$_1$, R$_2$, R$_3$ in this context is a $C_1$-$C_3$ alkyl group (including an isopropyl or t-butyl group). Additional optional substituents include: NHC(O)NH, (CH2)$_n$SH, (CH$_2$)$_n$O($C_1$-$C_6$ alkyl), (CH$_2$)$_n$C(O)($C_1$-$C_6$ alkyl), (CH$_2$)$_n$OC(O)($C_1$-$C_6$ alkyl), (CH$_2$)$_n$C(O)O($C_1$-$C_6$ alkyl), (CH)$_n$NHC(O)R$^1$, (CH$_2$)$_n$C(O)NR$_1$R$_2$, (OCH$_2$)$_n$OH, (CH$_2$O)$_n$COOH, $C_1$-$C_6$ alkyl, (OCH$_2$)$_n$O($C_1$-$C_6$ alkyl), (CH$_2$O)$_n$C(O)($C_1$-$C_6$ alkyl), (OCH$_2$)$_n$NHC(O)R$^1$, (CHO)$_n$C(O)NR$_1$R$_2$, S(O)$_2$R$^5$, and S(O)R$^5$ (R$^5$ is $C_1$-$C_6$ alkyl or a (CH$_1$)$_m$NR$_1$R$_2$ group). Each of the above-described groups may be linked directly to the substituted moiety or alternatively, the substituent may be linked to the substituted moiety (preferably in the case of an aryl or heteroaryl moiety) through an optionally substituted —(CH$_2$)$_m$— or, alternatively, an optionally substituted —(OCH$_2$)$_m$—, —(OCH$_2$CH$_2$)$_m$— or —(CH$_2$CH$_2$O)$_m$— group, which may be substituted with any one or more of the above-described substituents, wherein m is an integer from 1 to 20, e.g., 1 to 10 or 1 to 6. Alkylene groups —(CH$_2$)$_m$— or —(CR$_2$)$_m$— groups or other chains such as ethylene glycol chains, as identified above, may be substituted anywhere on the chain. As substituents can themselves be substituted, these groups also include, for example, such compound groups as aryl$C_1$-$C_6$alkyl (e.g., benzyl), halo$C_1$-$C_6$alkyl (e.g., trifluoromethyl), hydroxy$C_1$-$C_6$alkyl (e.g., 2-hydroxy-2-methylbutyl), and $C_1$-$C_6$alkyl-aryl (e.g., tolyl). Preferably, any optional substituent described herein (a "primary substituent") is itself optionally substituted with only one to three further substituents ("secondary substituents"), and each of said secondary substituents is optionally substituted with a single further substituent ("tertiary substituents").

It is understood that when describing the substituents attached in various positions to the core structure of Formula I, including substituents attached to substituents, in some cases, the substituent may be referred to using the name of the corresponding chemical compound, especially in the case of rings, whereas in some cases the same substituent may be referred to using the name of the corresponding chemical radical (e.g., having an "-yl" suffix), but these terms are interchangeable. For example, when referring to the substituent Ar, or a heteroaryl ring R attached to the substituent Ar, the terms "pyridine" and "pyridyl" are equivalent, as are the terms "morpholine" and "morpholinyl." The skilled artisan will recognize that such terms are used to denote attachment of, for example, pyridine or morpholine ring at the designated position, thus converting said ring to a pyridyl or morpholinyl substituent respectively. Absent an indication otherwise, such attachments may be made at any chemically permissible location of the attached ring.

As used herein, a range of carbon atoms which includes $C_0$ means that carbon is absent and is replaced with H (or deuterium). Thus, a range of carbon atoms which is $C_0$-$C_6$ includes carbons atoms of 1, 2, 3, 4, 5 and 6 and for C, H (or deuterium) stands in place of carbon.

Compounds of formula (I) may exist as tautomers, for example amide (NHC=O)↔hydroxyimine (N=COH) tautomers. Thus, it is understood that when R$^3$ is hydroxy (—OH) it is tautomerically equivalent to a keto group adjacent to a protonated nitrogen atom:

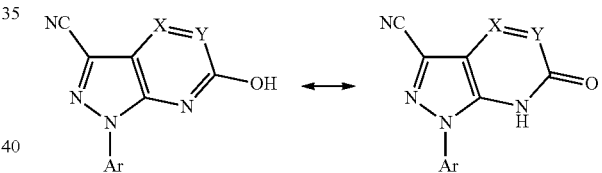

If X is —N— and Y is CR and R$^2$ is OH, or if Y is —N— and X is CR$^1$ and R$^1$ is OH, then similar tautomeric equivalents would be contemplated. Combinations of such groups is also within the scope of the present application, and such tautomeric equivalents are understood to be embraced. For example:

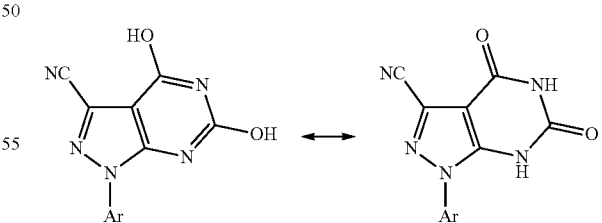

Exemplary non-limiting embodiments of the present disclosure are further described by reference to the following examples.

EXAMPLES

Unless otherwise noted, all starting materials and solvents were obtained from commercial sources (e.g., Acros Organics, Merck, Alfa Aesar, and TCI) and were used without further purification. All reactions were routinely monitored by thin-layer chromatography (TLC) performed on silica gel 60 F$_{254}$ (layer 0.2 mm) pre-coated aluminum foil (with fluorescent indicator UV254) (Sigma-Aldrich). Developed plates were air-dried and visualized under UV light (254/365 nm) or by using KMnO$_4$ solutions. Automated flash column chromatography was performed on pre-packed silica (50 Å, 20 μM) cartridges using Biotage® Selekt.

$^{1}$H NMR and $^{13}$C NMR spectra were recorded at 298K at 400 and 101 MHz, respectively, using a Bruker Avance 400 spectrometer by using residual solvent peak as internal standard. Chemical shifts are reported in ppm (δ) and the coupling constants (J) are given in Hertz (Hz). Peak multiplicities are abbreviated as follow: s (singlet), bs (broad singlet), d (doublet), dd (double doublet), t (triplet), dt (double triplet), q (quartet), p (pentet), and m (multiplet). Data were acquired using Bruker TopSpin software and processed using MestreNova software.

High-Resolution Mass Spectroscopy (HRMS) spectra were registered on Agilent Technologies 6540 UHD Accurate Mass Q-TOF LC-MS system or on Agilent 1290 Infinity Series U-HPLC system (Agilent Technologies, Santa Clara, CA, USA) coupled with a Q-TOF 6540 high-resolution mass spectrometer and 1290 Infinity Series DAD/UV-Vis detector (Agilent Technologies). The purity of the final compound was assessed as >98%, using UPLC-MS. The analyses were carried out according to the method listed below. The mobile phase was a mixture of water (solvent A) and acetonitrile (solvent B), both containing formic acid at 0.1%. Method: Phenomenex Luna Omega 1.6 μm Polar (C18, 100×2.1 mm) column at 40° C. using a flow rate of 0.65 mL/min in a 10 mm gradient elution. Gradient elution was as follows: 99.5:0.5 (A/B) to 5:95 (A/B) over 8 min, 5:95 (A/B) for 2 min, and then reversion back to 99.5:0.5 (A/B) over 0.1 min. The UV detection is an averaged signal from wavelength of 190 nm to 640 nm and mass spectra are recorded on a mass spectrometer using positive mode electro spray ionization.

Compounds described herein may be synthesized as described herein, using modified methods described herein or by methods known to a person of skill in the art.

Chemistry abbreviations: ACN, acetonitrile; Boc, tert-butoxycarbonyl; CD3OD, deuterated methanol; CDCl3, deuterated chloroform; DCE, dichloroethane; DCM, dichloromethane; DEE, diethyl ether; DIPEA, N,N'-diisopropylethylamine; DMA, dimethylacetamide; DMF, dimethylformamide; DMSO, dimethylsulfoxide; DMSO-d$_6$, deuterated dimethylsulfoxide; EA, ethyl acetate; h, hour; EtOH, absolute ethanol; Et3N, triethylamine; HATU, 2-(7-Aza-1H-benzotriazole-1-yl)-1,1,3,3-tetramethyluronium hexafluorophosphate; min, minutes; HRMS, high-resolution mass spectroscopy; MeOH, methanol; NMR, nuclear magnetic resonance; tBu, tert-butyl; tBuOH, tert-butanol; TLC, thin-layer chromatography; PE, petroleum ether; rt, room temperature.

Chemical Synthesis

Compounds of general formula (I) may be prepared by the following general synthetic approaches described below:

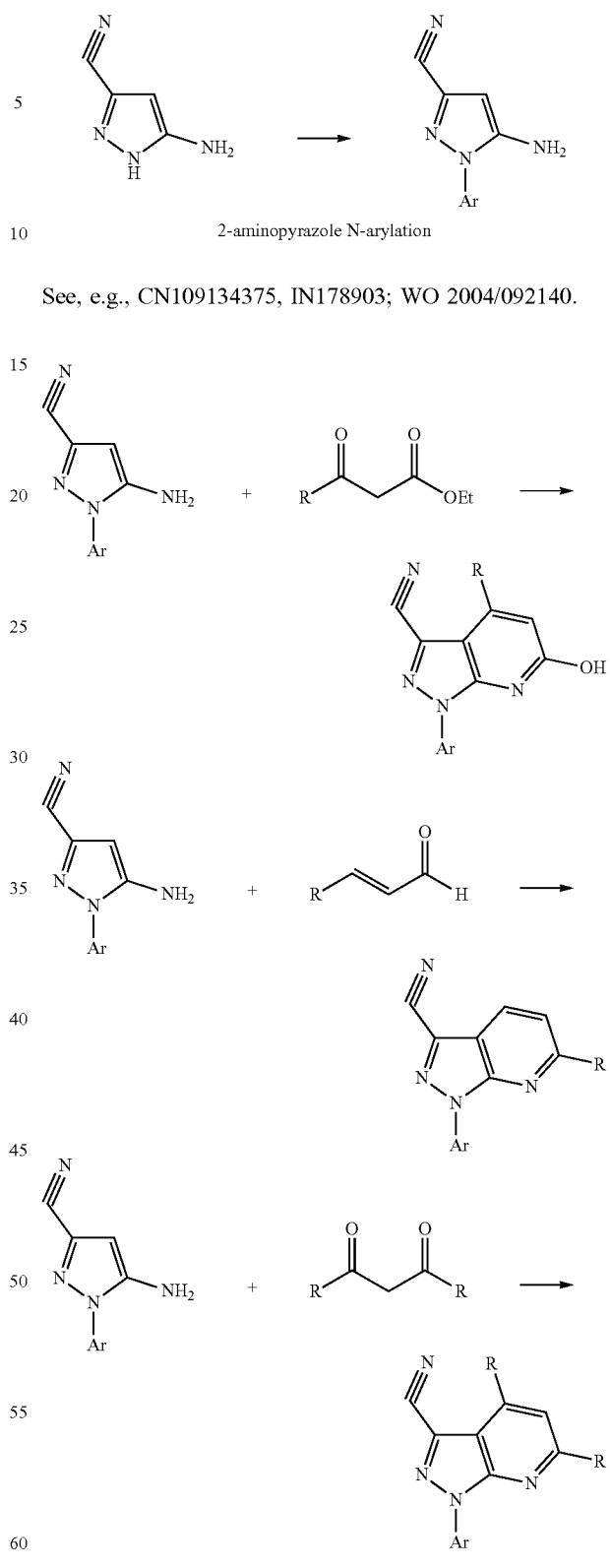

2-aminopyrazole N-arylation

See, e.g., CN109134375, IN178903; WO 2004/092140.

Heterocyclic Condensation

See, e.g., Silva et al., Eur. J Med. Chem., 46(9):4676-4681 (2011); Liu et al., Arch. Org. Chem, 2009(2): 258-268 (2009); de Mello et al., J Med Chem., 47(22): 5427-5432 (2004); El-Gohary & Shaaban, Eur. J. Med. Chem. 152(1):

126-136 (2018); Kurnar et al., *Org. Prep. Proc. Intl.,* 51(1): 1-89 (2019), Ibrahim et al., *J Ind. Chem. Soc.,* 64(6):345-347 (1987), Bhasvar et al., *J. Het. Chem.* 51(3):635-641 (2014); Toche et al., *J. Het. Chem.* 47(2):287-291 (2010);

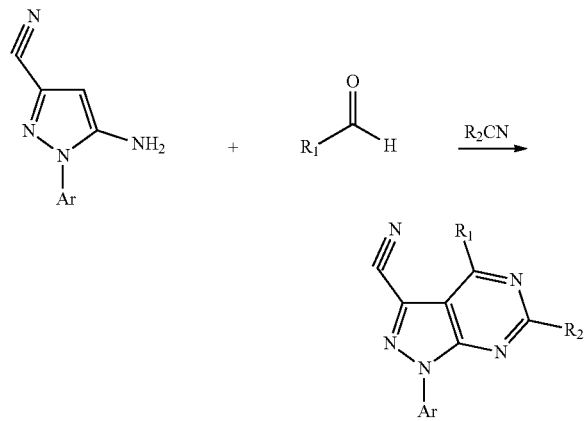

See, e.g., CN115304607, Grangurde et al., *J. Het. Chem.,* 51(4). 883-890 (2014); Abdelhamid, *J. Chem. Res. Synop.* 6:208-209 (1993); WO 2015/025025;

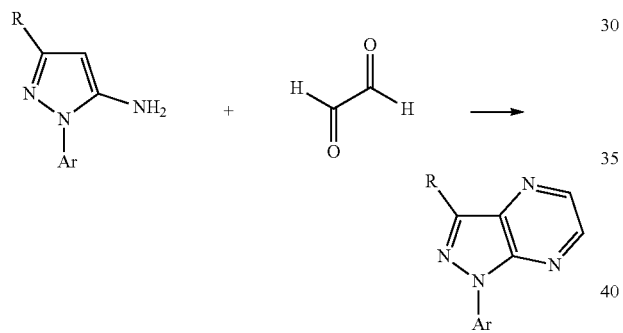

See, e.g., Chien et al., *Tet. Lett.* 45(21):4105-4108 (2004); Rizk et al., *Chin. J. Chem.,* 29(7):1451-1459 (2011); Farghaly et al., *Bioorg. & Med. Chem. Let.,* 22(7):2166-2175 (2014); Colombo et al., *J. Het. Chem.* 26(4):949-955 (1989).

Example 1: 1-(2,6-dichloro-4-(trifluoromethyl)phenyl)-6-hydroxy-4-(trifluoromethyl)-1H-pyrazolo[3,4-b]pyridine-3-carbonitrile

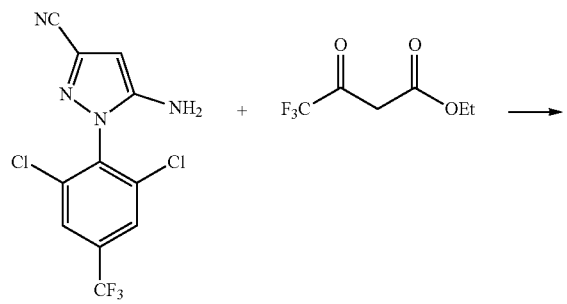

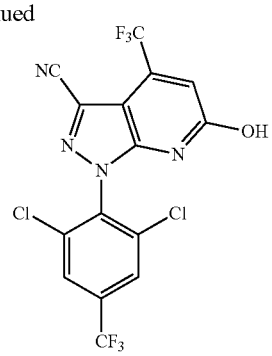

5-amino-1-(2,6-dichloro-4-(trifluoromethyl)phenyl)-1H-pyrazole-3-carbonitrile (commercially available) (0.100 g, 0.311 mmol) and ethyl 4,4,4-trifluoro-3-oxobutanoate (commercially available) (0.115 g, 0.091 μL, 0.623 mmol) are stirred in a pre-warmed pressure tube at 150° C. for 18 h. After cooling, the crude product is purified by automated flash chromatography on silica gel (4 g cartridge, gradient petroleum ether/ethyl acetate 99:1 to 70:30) to afford the title compound (36 mg, 26% yield) as white solid. $^1$H NMR (400 MHz, DMSO-d$_6$) δ 13.36 (bs, 1H), 8.40 (s, 2H), 7.34 (s, 1H); $^{13}$C NMR (101 MHz, DMSO-d$_6$) δ 166.50-166.26 (m) 151.26, 136.07 (2C), 135.36, 134.05 (q, J=34.1 Hz), 13247 (q, J=35.9 Hz), 127.38-127.22 (m), 122.61 (q, J=274.0 Hz), 122.15 (q, J=273.4 Hz), 119.16, 112.26, 110.54, 104.49; $^{19}$F NMR (376 MHz, DMSO-d$_6$) δ -61.38, -61.52. HRMS (ESI) m/z [M+Na]+ calcd for $C_{15}H_4Cl_2F_6N_4O$ 462.95586, found 462.95666.

Comparative Example 2: N-(3-cyano-1-(2,6-dichloro-4-(trifluoromethyl)phenyl)-1H-pyrazol-5-yl) acetamide

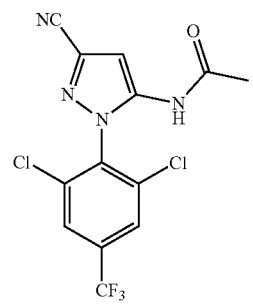 [SMILES: CC(=O)Nc1cc(C#N)nn1-c1c(Cl)cc(C(F)(F)F)cc1Cl]

To a solution of 5-amino-1-(2,6-dichloro-4-(trifluoromethyl)phenyl)-1H-pyrazole-3-carbonitrile (commercially available) (0.100 g, 0.311 mmol) in acetic acid (3.0 mL), is added ethyl 4,4,4-trifluoro-3-oxobutanoate (commercially available) (0.057 g, 0.045 μL, 0.311 mmol) and the mixture is stirred at 120° C. for 24 h. After cooling, the solvent is evaporated and the crude product is purified by automated flash chromatography on silica gel (4 g cartridge, gradient petroleum ether/ethyl acetate 80:20) to afford the title compound (46 mg, 41% yield) as white solid. $^1$H NMR (400 MHz, DMSO-d$_6$) δ 10.45 (s, 1H), 8.33 (s, 2H), 7.21 (s, 1H), 2.03 (s, 3H); $^{13}$C NMR (101 MHz, DMSO-d$_6$) δ 168.28, 140.91, 136.02 (2C), 135.98, 133.57 (q, d=33.8 Hz), 127.13 (q, J=33.8 Hz), 126.87, 122.76 (q, J=274.0 Hz), 114.08, 101.49, 23.51; $^{19}$F NMR (376 MHz, DMSO-d$_6$) δ -61.42.

49

HRMS (ESI) m/z [M+Na]+ calcd for $C_{13}H_7Cl_2F_3N_4O$ 384.98412, found 384.98409.

Comparative Example 3: N-(3-cyano-1-(2,6-dichloro-4-(trifluoromethyl)phenyl)-1H-pyrazol-5-yl)propionamide

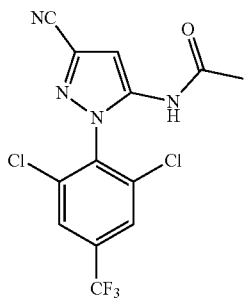 [SMILES: CC(=O)Nc1cc(C#N)nn1-c1c(Cl)cc(C(F)(F)F)cc1Cl]

To a solution of 5-amino-1-(2,6-dichloro-4-(trifluoromethyl)phenyl)-1H-pyrazole-3-carbonitrile (commercially available) (0.200 g, 0.623 mmol) in propionic acid (1.5 mL), is added ethyl 4,4,4-trifluoro-3-oxobutanoate (commercially available) (0.126 g, 0.100 L, 0.685 mmol) and the mixture is stirred at 120° C. for 24 h. After cooling, the solvent is evaporated and the crude product is purified by automated flash chromatography on silica gel (4 g cartridge, gradient petroleum ether/ethyl acetate 80:20) to afford the title compound (35 mg, 15% yield) as white solid. $^1$H NMR (400 MHz, DMSO-$d_6$) δ 10.40 (s, 1H), 8.33 (s, 2H), 7.22 (s, 1H), 2.29 (q, J=7.5 Hz, 2H), 1.00 (t, J=7.5 Hz, 3H); $^{13}$C NMR (101 MHz, DMSO-$d_6$) δ 172.02, 140.94, 136.03, 135.99 (2C), 133.52 (q, J=33.8 Hz), 127.22-12701 (i), 126.84, 122.77 (q, J=273.9 Hz), 114.12, 101.61, 28.99, 9.65; $^{19}$F NMR (376 MHz, DMSO-$d_6$) δ −61.40. HRMS (ESI) m/z [M+H]+ calcd for $C_{14}H9Cl2F3N4O$ 377.01783, found 377.01823.

Example 4: 1-(2,6-dichloro-4-(trifluoromethyl)phenyl)-4-(difluoromethyl)-6-hydroxy-1H-pyrazolo[3,4-b]pyridine-3-carbonitrile

50

-continued

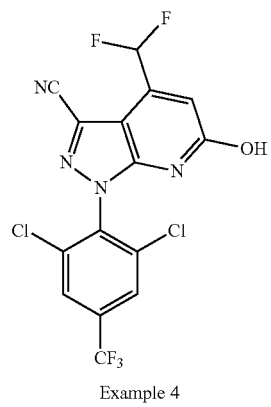

Example 4

5-amino-1-(2,6-dichloro-4-(trifluoromethyl)phenyl)-1H-pyrazole-3-carbonitrile (0.050 g, 0.155 mmol) and ethyl 4,4-difluoro-3-oxobutanoate (0.027 µL, 0.187 mmol) are stirred in a pressure tube in a pre-warmed bath at 150° C. for 1 h. Then, $CF_3COOH$ (0.012 µL, 0.155 mmol) is added and the mixture is left stirring in the pressure tube at 150° C. overnight. After cooling, the crude product is purified by automated flash chromatography on silica gel (4 g cartridge, gradient PE:EA from 99:1 to 70:30) to afford the title compound (12 mg, 11% yield) as a light-yellow solid. $^1$H NMR (400 MHz, DMSO-$d_5$) δ 13.02 (bs, 1H), 8.40 (s, 2H), 7.46 (t, J=53.9 Hz, 1H), 7.15 (s, 1H); $^{19}$F NMR (376 MHz, DMSO-$d_6$) δ −61.50, −112.70, −112.84. HRMS (ESI) m/z [M−H]− calcd for $C_{15}H_5Cl_2F_5N_4O$ 420.96878, found 420.96900.

Examples 5-16

Additional compounds within the scope of the disclosure can be made according to the following general scheme:

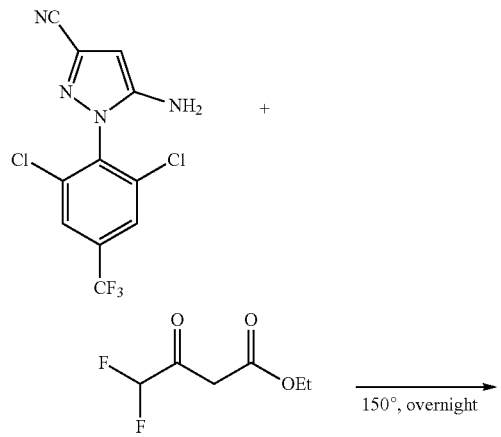

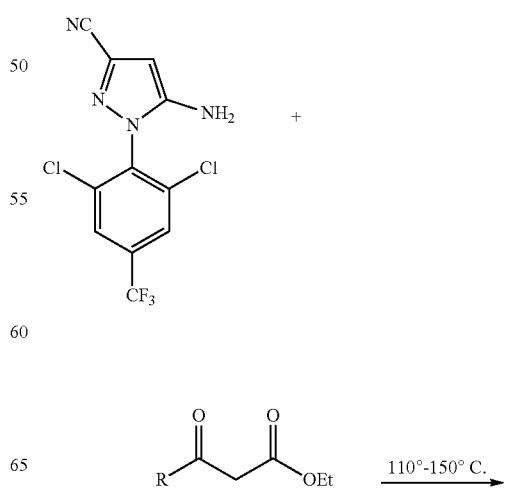

-continued

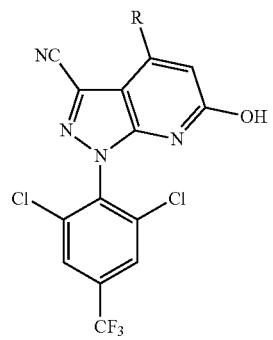

R = CH₂F, CH₂Cl, CH₃, CD₃, CH(CH₃)₂, cyclopropyl
R = CF₂Cl, CF₂CH₃, CF₂BR, CCl₃, CHCl₂, CHClF The following compounds are made according to procedures analogous to that shown for Examples 1 and 4:

| Example No. | Structure | IUPAC name |
|---|---|---|
| Example 5 | 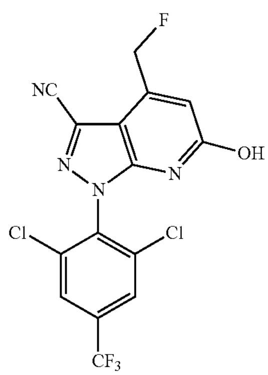 [SMILES: N#Cc1nn(-c2c(Cl)cc(C(F)(F)F)cc2Cl)c2nc(O)cc(CF)c12] | 1-(2,6-dichloro-4-(trifluoromethyl)phenyl)-4-(fluoromethyl)-6-hydroxy-1H-pyrazolo[3,4-b]pyridine-3-carbonitril |
| Example 6 | 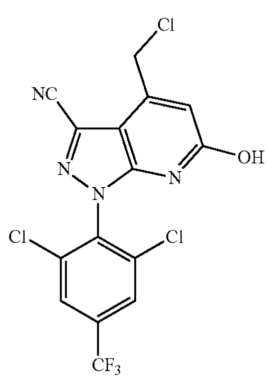 [SMILES: N#Cc1nn(-c2c(Cl)cc(C(F)(F)F)cc2Cl)c2nc(O)cc(CCl)c12] | 4-(chloromethyl)-1-(2,6-dichloro-4-(trifluoromethyl)phenyl)-6-hydroxy-1H-pyrazolo[3,4-b]pyridine-3-carbonitrile |

| Example No. | Structure | IUPAC name |
| --- | --- | --- |
| Example 7 | 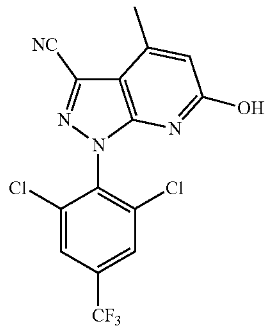 [SMILES: Cc1cc(O)nc2c1c(C#N)nn2-c1c(Cl)cc(C(F)(F)F)cc1Cl] | 1-(2,6-dichloro-4-(trifluoromethyl)phenyl)-6-hydroxy-4-methyl-1H-pyrazolo[3,4-b]pyridine-3-carbonitrile |
| Example 8 | 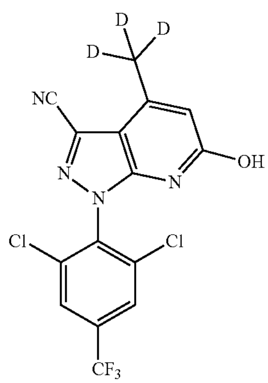 [SMILES: [2H]C([2H])([2H])c1cc(O)nc2c1c(C#N)nn2-c1c(Cl)cc(C(F)(F)F)cc1Cl] | 1-[2,6-dichloro-4-(trifluoromethyl)phenyl]-6-hydroxy-4-methyl-d$_3$-1H-pyrazolo[3,4-b]pyridine-3-carbonitrile |
| Example 9 | 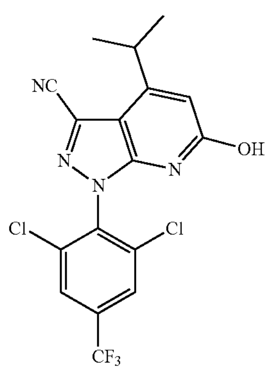 [SMILES: CC(C)c1cc(O)nc2c1c(C#N)nn2-c1c(Cl)cc(C(F)(F)F)cc1Cl] | 1-(2,6-dichloro-4-(trifluoromethyl)phenyl)-6-hydroxy-4-isopropyl-1H-pyrazolo[3,4-b]pyridine-3-carbonitrile |
| Example 10 | 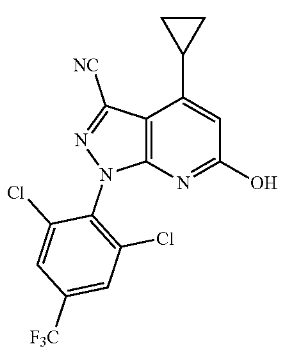 [SMILES: N#Cc1nn(-c2c(Cl)cc(C(F)(F)F)cc2Cl)c2nc(O)cc(C3CC3)c12] | 4-cyclopropyl-1-(2,6-dichloro-4-(trifluoromethyl)phenyl)-6-hydroxy-1H-pyrazolo[3,4-b]pyridine-3-carbonitrile |

-continued

| Example No. | Structure | IUPAC name |
| --- | --- | --- |
| Example 11 | 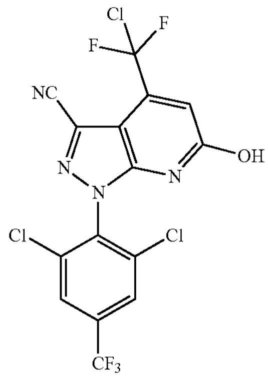 [SMILES: N#Cc1nn(-c2c(Cl)cc(C(F)(F)F)cc2Cl)c2nc(O)cc(C(F)(F)Cl)c12] | 4-(chlorodifluoromethyl)-1-(2,6-dichloro-4-(trifluoromethyl)phenyl)-6-hydroxy-1H-pyrazolo[3,4-b]pyridine-3-carbonitrile |
| Example 12 | 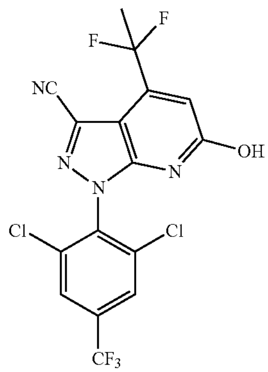 [SMILES: CC(F)(F)c1cc(O)nc2c1c(C#N)nn2-c1c(Cl)cc(C(F)(F)F)cc1Cl] | 1-(2,6-dichloro-4-(trifluoromethyl)phenyl)-4-(1,1-difluoroethyl)-6-hydroxy-1H-pyrazolo[3,4-b]pyridine-3-carbonitrile |
| Example 13 | 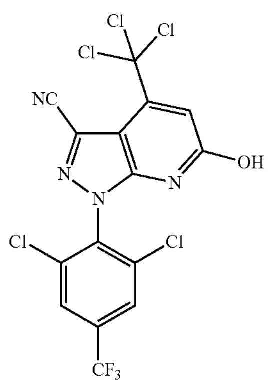 [SMILES: N#Cc1nn(-c2c(Cl)cc(C(F)(F)F)cc2Cl)c2nc(O)cc(C(Cl)(Cl)Cl)c12] | 1-(2,6-dichloro-4-(trifluoromethyl)phenyl)-6-hydroxy-4-(trichloromethyl)-1H-pyrazolo[3,4-b]pyridine-3-carbonitrile |
| Example 14 | 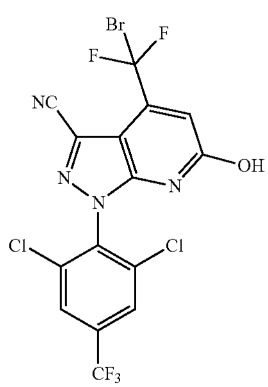 [SMILES: N#Cc1nn(-c2c(Cl)cc(C(F)(F)F)cc2Cl)c2nc(O)cc(C(F)(F)Br)c12] | 4-(bromodifluoromethyl)-1-(2,6-dichloro-4-(trifluoromethyl)phenyl)-6-hydroxy-1H-pyrazolo[3,4-b]pyridine-3-carbonitrile |

| Example No. | Structure | IUPAC name |
|---|---|---|
| Example 15 | 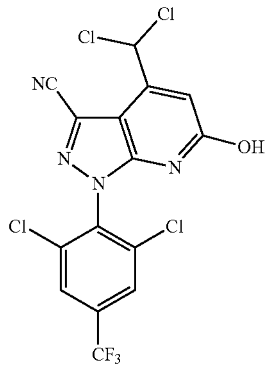 [SMILES: N#Cc1nn(-c2c(Cl)cc(C(F)(F)F)cc2Cl)c2nc(O)cc(C(Cl)Cl)c12] | 1-(2,6-dichloro-4-(trifluoromethyl)phenyl)-4-(dichloromethyl)-6-hydroxy-1H-pyrazolo[3,4-b]pyridine-3-carbonitrile |
| Example 16 | 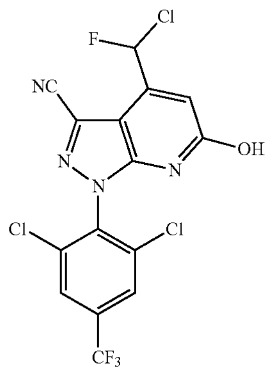 [SMILES: N#Cc1nn(-c2c(Cl)cc(C(F)(F)F)cc2Cl)c2nc(O)cc(C(F)Cl)c12] | 4-(chlorofluoromethyl)-1-(2,6-dichloro-4-(trifluoromethyl)phenyl)-6-hydroxy-1H-pyrazolo[3,4-b]pyridine-3-carbonitrile |

Example 17: In Vivo Evaluation

To explore the therapeutic potential of the compounds of the present disclosure, live chickens with mite infestation (*Dermanyssus gallinae*) are treated topically with solutions of test compound, with Fipronil as a positive control. Test solutions are prepared by dissolving the test compound in a mixture of 2-butoxyethanol, ethanol, and water (7:2:1) to reach a final concentration of 0.25% (w/v).

The test solution is administered using a mechanical spray pump delivering 0.5 mL of solution per actuation. The test solution is sprayed over the entire surface of the animal's body from a distance of 10-20 centimeters, resulting in direct contact of the solution with the animal's skin. The dosage applied to each animal is 3 mL/kg, equivalent to 7.5 mg/kg (kg live weight). The dosage is achieved using six actuations of the spray per kg of body weight per day. The treatment is administered once daily for 5 days at 24 hours intervals. One animal is left untreated as a negative control.

Blood samples are taken from each animal before the first treatment (T=0), and at 24-hour intervals thereafter. Each egg produced after a treatment is collected for later analysis.
Plasma Concentration Analysis Plasma samples are derived from each blood sample using standard procedures immediately after blood collection. Plasma is stored frozen at −80° C. until the time of analysis. Samples are then thawed at room temperature and extraction is performed by solid phase extraction (SPE) (Strata-X 33. Polymeric Reversed Phase, 60 mg/3 mL, Phenomenex) on an aliquot of sample (100 μl) pretreated for protein precipitation with 300 μl of acetonitrile. After protein precipitation, the samples are well vortexed and then centrifuged (12000 rpm, 10 min, RT). Supernatant is collected and transferred to clean Falcon tubes and diluted with 3 ml of water. Strata-X columns are conditioned with 2 ml of methanol and with 2 ml of water. Samples are loaded after conditioning, and the columns are washed with 2 ml of water, and analytes are eluted with 2 nil of methanol, dried under nitrogen and then resuspended in 100 μl of acetonitrile for mass spectral analysis. The recovery of the method is calculated by adding standards to not-treated plasma and it is found to be 72%; calibration curves were made for both compounds (0.005-10 μM).

A Thermo Q-exactive mass spectrometer (Thermo Fisher Scientific, Waltham, MA) is used. The LC system, governed by Chromeleon X-press software, consists of a binary pump, a thermostated autosampler, and a column compartment, all Dionex Ultimate 3000 series modules (Thermo Fisher Scientific, Waltham, MA). A volume of 2 μL is injected for each sample. Chromatographic separation of analytes is conducted in reverse-phase chromatography. A Luna Omega 1.6 μm Polar (CIS, 2.1 mm×100 mm) is used, and the mobile phases are (A) water and (B) acetonitrile, both containing 0.1% v/v formic acid. The flow rate is 0.400 mL/min over a 12 minute gradient elution as follows: 99.5:0.5 (A/B) to 5:95 (A/B) over 10 minutes, 5:95 (A/B) for 2 minutes, and then reversion back to 99.5:0.5 (A/B) over 2.5 minutes. The column is operated at a constant temperature of 40° C. The LC effluents are introduced into the Q-Exactive mass spectrometer by an H-ESI source operating in the negative mode with a sheath gas flow rate of 45; an auxiliary gas flow rate of 15; a spray voltage of 3.5 kV; capillary temperature and auxiliary gas heater temperature, respectively, of 320 and 350° C.; and S-lens RF level 50. The Q-Exactive mass spectrometer is operated with a resolution of 140.000 in FullMS mode. Data analysis is performed using Qual Browser Thermo Xalibur 4.0.27.13 (Thermo Fisher Scientific) and Lipostar 2.0 (Molecular Discovery ltd) software.

The following peaks are observed and quantified: Fipronil, RT 9.54 min ([M–H]– ion 434.9318 m/z); Fipronil sulfone, RT 9.98 min ([M–H]– ion 450.9268 m/z); Fipronil amide, RT 9.97 min ([M–H]– ion 452.9235 m/z); Compound of Example 1, RT 9.95 min ([M–H]– ion 438.9602 m/z) No metabolites of the Compound of Example 1 are observed.

Plasma Results

Plasma from four chickens is analyzed, two chickens treated with Fipronil and two treated with the Compound of Example 1. Plasma samples from Day 3 and Day 5 are analyzed. The day 3 plasma samples from Chicken 1 were found to be unusable due to inhomogeneity. The results are shown in the following tables:

| Fipronil Treatment | | | | |
|---|---|---|---|---|
| Analyte: | Chicken 1 3 days | Chicken 1 5 days | Chicken 2 3 days | Chicken 2 5 days |
| Fipronil | n.d. | 2.8 ppm | 1.1 ppm | 1.5 ppm |
| Fipronil Sulfone | n.d. | 3.7 ppm | 1.4 ppm | 1.8 ppm |
| Fipronil Amide | n.d. | Trace | Trace | Trace |
| Fipronil Total | n.d. | 6.5 ppm | 2.5 ppm | 3.3 ppm |

| Compound of Example 1 Treatment | | | | |
|---|---|---|---|---|
| Analyte: | Chicken 3 3 days | Chicken 3 5 days | Chicken 4 3 days | Chicken 4 5 days |
| Ex. 1 | 0.01 ppm | 0.03 ppm | 0.7 ppm | 1.2 ppm |

The results demonstrate that the Compound of Example 1 undergoes substantially less systemic absorption and plasma accumulation compared to Fipronil.

Egg Concentration Analysis

A modified and optimized QuEChERS protocol was employed to extract the compounds from eggs. The shell is manually removed, and then each egg is transferred to a clean beaker and homogenized with an electric mixer for small volumes. 5 grams of homogenized egg is put into a 50 mL Falcon tube, and 5 mL of water is added and the samples are shaken for 10 minutes. Next, 10 mL of acetonitrile is added and the samples are shaken again for 10 minutes. Then the roQ salts (4.0 g MgSO4, 1.0 g NaCl, 1.0 SCTD and 0.5 g SCDS, Phenomenex P/N KS08909) are added to each sample, and the mixture is well shaken for 10 minutes. Samples are then centrifuged at 2500 g for 5 minutes at room temperature, and the supernatant is transferred to an HPLC vial for analysis. The same HPLC-MS method is used as described above.

Egg Results

One egg from two chickens is analyzed: one chicken treated with Fipronil and one chicken treated with the Compound of Example 1. The eggs are both from Day 5. The results are shown in the following tables expressed as relative LC-MS peak area:

| Fipronil Treatment | |
|---|---|
| Analyte: | Chicken 1 5 days |
| Fipronil | 4.8 |
| Fipronil Sulfone | 5.6 |
| Fipronil Amide | 3.8 |
| Fipronil Total | 14.2 |

| Compound of Example 1 Treatment | |
|---|---|
| Analyte: | Chicken 2 5 days |
| Ex. 1 | 3.0 |

The results demonstrate that the Compound of Example 1 undergoes substantially less accumulation in the eggs of treated chickens compared to Fipronil.

Antiparasitic Efficacy

To test the effectiveness of the chemical compounds, live chickens with natural mite infestation (*Dermanyssus gallinae*) are treated topically with solutions of test compound, with Fipronil as a positive control. Test solutions are prepared by dissolving the test compound in a mixture of 2-butoxyethanol, ethanol, and water (7:2:1) to reach a final concentration of 0.25% (w/v). The test solutions are sprayed on the animals from the bottom up, to facilitate their application and skin penetration, using a mechanical spray pump delivering 0.5 mL of solution per actuation. The dosage applied to each animal is 3 mL/kg, equivalent to 7.5 mg/kg (kg live weight). The dosage is achieved using six actuations of the spray per kg of body weight per day. The treatment is administered once daily for 5 days at 24 hours intervals.

Two animals are treated with the compound of Example 1, and two animals are treated with Fipronil, while one animal is left untreated as a negative control. The infestation by *D. gallinae* is monitored by checking the density of mites in particular areas of the animal's bodies (feet, legs, and wings), comparing pre-treatment levels of infestation to post-treatment levels.

When all pests have been eliminated, a 100% pest control capability was achieved. In the case of some chemical products, when the pest was not fully eliminated, the disinfestation capacity was measured by averaging the number of infesting organisms located in three distinct areas of the treated animals, at the beginning of the treatment, and at the end of the treatment.

By day 5 of treatment, all chickens treated with either the Compound of Example 1 or Fipronil were 100% free of mites. Untreated chickens (negative control) retained substantial amounts of mites similar to the initial amounts.

The experiments are repeated using the compounds of Example 2 and 3 as comparative examples. After five days of treatment, levels of mite infestations are reduced by only about 5-10%, which could be explained by non-specific solvent effects on the mites.

Example 18: Metabolic Stability

As discussed earlier, phenylpyrazole insecticides suffer from issues and concerns related to their degradation. While environmental degradation of phenylpyrazoles, such as fipronil, is slow, metabolic degradation in animals is rapid. Moreover, the primary metabolites of fipronil, the sulfone, the sulfide, and the desulfinylated derivative, are considerably more toxic, persistent, bioaccumulative, and less selective than the parent compound. See Leemans et al.

The metabolic stability of the Compounds of Examples 1 and 4 is therefore evaluated to determine whether metabolic degradation results in metabolites of concern.

Briefly, Human Cryopreserved Hepatocytes (Gibco, lot. HUE125) are added to incubation wells in a 96-well assay plate at a density of 500,000 cells/mL in William's E Medium. The test substrates (compound of Example 1 or 4) are added to the wells at a final concentration of 1 μM. The wells are incubated at 37° C. and stop solution is added to wells at time points: 0, 30, 60, 120, 240 min. The stop solution is ice-cold solution containing 0.5 μM labetalol in acetonitrile (100 μL/well) (2:1, vol/vol). Each time point is tested in triplicate. Analysis is carried out by LC-MS.

LC-MS Conditions:
Instrument: QExactive
Column: Luna Omega 1.6 μm polar C18 100 Å (150×2.1 mm)
Column temperature: 40° C.
Column No: 102+pre-column installed
Injection volume: 2 μl
Flux: 0.40 mL/min
Polarity: Negative
Fluent A: water Milli Q+0.1% FA
Fluent B: ACN+0.1% FA
Acquisition method: Full MS+DDS on the IL obtained with MassMetaSite (peak others ON).

It is found that the compound of Example 1 is metabolically stable. After 240 minutes, approximately 95.5% of the original compound of Example 1 (RT 11.12 min) is still present, and no particular peaks indicative of metabolites is observed.

It is found that the compound of Example 4 is highly metabolically stable. After 240 minutes, approximately 84.2% of the original compound of Example 4 is still present (RT 10.65), with one major metabolite (RT 9.02, M+176) rising to a peak level of 1%. The apparent molecular weight of the metabolite is consistent with N-glucuronidation of the keto tautomer of the 2-hydroxypyridine ring.

Example 19: Acute Honeybee Toxicity

The acute oral toxicity and acute contact toxicity effects of the Compound of Example 1, and fipronil, are determined in adult worker honeybees, *Apis mellifera* L The study is carried out in accordance with OECD Guidelines 213 (oral toxicity) and 214 (contact toxicity) (September 1998).

In accordance with OECD Test Guidelines No. 213 and 214, the test is considered valid if: (1) the average mortality of the control groups is ≤10% at the end of the test; and the average, control-corrected mortality of the reference item groups is ≥50% at the end of the test, at the tested dose (internal validity criteria according to POS BT200).

Young *Apis mellifera* L. worker honeybees are randomly collected in the morning of use or the day before from an adequately fed, healthy diseases-free and queen right beehive, not treated with chemical substances. Hives from an established apiary colony are used, and the colonies are inspected periodically, according to standard bee-keeping practices. All colonies are kept outside under field conditions and bees collect food from the environment. The last treatment against *Varroa* mites was done in November 2023.

The bees are fed ad libitum with a water sucrose solution 50% w/v (or 500 g/L), prepared with tap water.

Acute Oral Toxicity Test

Adult worker honeybees are exposed to three increasing doses of the test item (see Table 1) dispersed in a 50% (w/v) aqueous sucrose solution, for a maximum of 6 hours (see section 4.5.1).

Untreated 50% w/v sucrose solution with 0.2% of propanol-water solution (ratio 80%-20%) is used as a negative control.

Bee mortality is recorded after 4, 24 and 48 hours, and compared with the control value. If the mortality rate increases by more than 10% between 24 and 48 hours, whilst the control mortality rate remains ≤10%, the test is extended to a maximum of 96 hours.

The test item is diluted with aqueous sucrose solution 50% (w/v) to prepare the oral solutions. The bees used for the oral test are anesthetized with carbon dioxide for the time necessary to immobilize them and placed inside the test cages; 2 hours before the treatment they are starved. A volume of 200 μL (20 μL/bee) of treated diet is administered to each cage with a dispenser (e.g., a syringe without tip), weighed before and after filling.

The overall exposure period is 6 hours, during which consumption is monitored: the feeder is changed at the end of the six hours or once the treated diet has been consumed (usually within 3-4 hours). In both cases, the feeder is weighed and a new feeder with untreated 50% (w/v) sucrose solution is provided ad libitum, and the mean effective dose is calculated based on the actual consumption.

Acute Contact Toxicity Test

Adult worker honeybees are exposed to three increasing doses of the test item (see Table 2) by direct application to the thorax (droplets, see section 4.5.2). One control group is treated with propanol-water solution (ratio 80%-20%) in addition to test item groups.

Bee mortality is recorded after 4, 24 and 48 hours, and compared with the control value. If the mortality rate increases by more than 10% between 24 and 48 hours, whilst the control mortality rate remains ≤10%, the is extended to a maximum of 96 hours.

The test item is diluted in propanol-water solution (ratio 80%-20%) to prepare the contact solutions.

The bees used for the contact test are anaesthetized with carbon dioxide and individually treated by topical application of 2 μL of the test solutions onto the thorax using a micro applicator. The honeybees are then be moved to the cages and fed ad libitum with sucrose solution.

Experimental Design

TABLE 1

Oral test trial layout

| Groups | Doses[1] (μg product/bee) | Concentration (g product/L diet) | Number of Bees/cage | Replicates |
|---|---|---|---|---|
| Propanol Control | — | — | 10 | 3 |
| Test item (T1) | 0.002 | 0.0001 | 10 | 3 |
| Test item (T2) | 0.004 | 0.0002 | 10 | 3 |
| Test item (T3) | 0.006 | 0.0003 | 10 | 3 |

[1]200 μL of oral solution (20 μL/bee) is administered to each replicate (cage).

TABLE 2

Contact test trial layout

| Groups | Doses[1] (μg product/bee) | Concentration (g product/L diet) | Number of Bees/cage | Replicates |
|---|---|---|---|---|
| Propanol Control | — | — | 10 | 3 |
| Test item (T1) | 0.002 | 0.001 | 10 | 3 |
| Test item (T2) | 0.004 | 0.002 | 10 | 3 |
| Test item (T3) | 0.006 | 0.003 | 10 | 3 |

[1] A treatment volume of 2 μL/bee is used for the control, the test item and the reference item.

Disposable and well-ventilated cages with an internal volume not lower than 200 cm$^3$ are used. Each cage is equipped with a transparent lid, for a suitable observation of the bees from outside. The upper side of the cage has at least one hole for inserting the feeder: a syringe filled of 50% (w/v) aqueous sucrose solution is inserted in one hole.

The tests are conducted under the following conditions: (a) Temperature: 25.00±200° C.; (b) Relative humidity: 60.00±10 00%, The honeybees are kept under constant darkness except during the assessments. Throughout the experimental phase, the temperature and relative humidity is continuously recorded with a dedicated data-logger with sensors located close to the test units.

The tests last 48 hours. If mortality of the test item-treated group continues to rise by more than 10% after the first 24 hours, then the test duration is extended to a maximum of 96 hours, provided that control mortality does not exceed 10%.

The number of dead honeybees per cage is recorded after 4, 24 and 48 hours. If a prolonged observation period is required, further assessments are made every 24 hours, tip to a maximum duration of 96 hours. The amount of diet consumed per group is quantitatively estimated if treated diet will be left after 6 hours of exposure.

Any behavioral differences between the honeybees of the control group(s) and those of the test item group are recorded as follows:

TABLE 3

Test system behavioral states description

| | |
|---|---|
| Live: | alive and apparently unaffected |
| Affected: | uncoordinated movement, increased rate of grooming or constant grooming, lethargy, lack of feeding, diarrhea |
| Moribund: | on their back or side, still twitching, but generally unable to slue themselves |
| Dead: | no longer moving |

Results

Data is summarized in tabular form, showing the number of live, dead and abnormal bees per experimental group. The mortality of each replicate is calculated as a percentage, comparing the number of dead bees to those introduced at the beginning. The mean value of the treated group is compared to the mean mortality of the respective control group(s) using the Abbott's formula modified by Schneider-Orelli (POS BT 200):

$$CM\% = \left(\frac{Mt - Mc}{100 - Mc}\right) \times 100$$

$CM$ = mean corrected mortality (%)

$Mc$ = mean mortality in the control group (%)

$Mt$ = mean mortality in the treated group (%)

TABLE 4

Compound of Example 1

Oral Toxicity

| Group | Dose (μg/bee) | Mean Consumption Rate | % CM (4 hours) | % CM (24 hours) | % CM (48 hours) |
|---|---|---|---|---|---|
| T1 | 0.002 | 98.7% | 0.0 | 0.0 | 0.0 |
| T2 | 0.004 | 99.1% | 0.0 | 19.2 | 17.4 |
| T3 | 0.006 | 99.8% | 0.0 | 15.4 | 13.0 |

Contact Toxicity

| Group | Dose (μg/bee) | % CM (4 hours) | % CM (24 hours) | % CM (48 hours) |
|---|---|---|---|---|
| T1 | 0.002 | 0.0 | 7.1 | 0.0 |
| T2 | 0.004 | 0.0 | 0.0 | 0.0 |
| T3 | 0.006 | 0.0 | 50.0 | 57.7 |

TABLE 5

Fipronil

Oral Toxicity

| Group | Dose (μg/bee) | Mean Consumption Rate | % CM (4 hours) | % CM (24 hours) | % CM (48 hours) |
|---|---|---|---|---|---|
| T1 | 0.002 | 98.3% | 0.0 | 20.8 | 23.8 |
| T2 | 0.004 | 99.6% | 0.0 | 37.5 | 33.3 |
| T3 | 0.006 | 99.0% | 3.3 | 58.3 | 66.7 |

Contact Toxicity

| Group | Dose (μg/bee) | % CM (4 hours) | % CM (24 hours) | % CM (48 hours) |
|---|---|---|---|---|
| T1 | 0.002 | 0.0 | 7.1 | 7.7 |
| T2 | 0.004 | 0.0 | 25.0 | 30.8 |
| T3 | 0.006 | 0.0 | 71.4 | 76.9 |

The results demonstrate that compounds according to the invention are substantially less toxic to honeybees than fipronil is.

The Examples provided herein are exemplary only and are not intended to be limiting in any way to the various aspects and embodiments of the invention described herein.

What is claimed is:

1. A compound having the following general structure,

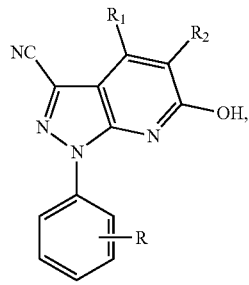

wherein $R^1$ and $R^2$ are each independently selected from H, halo, cyano, nitro, hydroxy, amino, $C_{1-6}$alkyl, $C_{3-6}$cycloalkyl, $C_{1-6}$haloalkyl, $C_{1-6}$alkoxy, $C_{1-6}$haloalkoxy, $C_{3-6}$cycloalkoxy, $C_{3-6}$halocycloalkyl, $NH(C_{1-6}$alkyl), $N(C_{1-6}$alkyl)($C_{1-6}$alkyl), and 3-6 membered heterocycloalkyl; and each R is independently selected from halo, cyano, nitro, hydroxy, amino, $C_{1-6}$alkyl, $C_{3-6}$cycloalkyl, $C_{1-6}$haloalkyl, $C_{1-6}$alkoxy, $C_{1-6}$haloalkoxy, and $C_{3-6}$halocycloalkyl;

in free or salt form.

2. The compound according to claim 1, wherein $R^1$ is selected from halo, cyano, $C_{1-3}$alkyl, and $C_{1-3}$haloalkyl.

3. The compound according to claim 1, wherein $R^2$ is selected from H, halo, and cyano.

4. The compound according to claim 1, wherein the phenyl ring is substituted by one, two, or three groups R.

5. The compound according to claim 1, wherein the compound is of the following general structure,

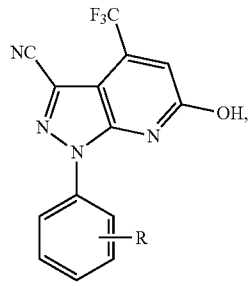

wherein R is as defined in claim 1.

6. The compound according to claim 1, wherein each R is independently selected from halo, cyano, nitro, hydroxy, $C_{1-6}$haloalkyl, $C_{1-6}$haloalkoxy, and $C_{3-6}$halocycloalkyl.

7. The compound according to claim 1, wherein the R-substituted phenyl ring is selected from 2,6-dichloro-4-trifluoromethylphenyl, 2,6-dichloro-4-trifluoromethoxyphenyl, 2,6-dichloro-4-bromophenyl, 2,6-dichloro-4-difluoromethylphenyl, 2,6-dichloro-4-difluoromethoxyphenyl, 2,6-dichloro-4-fluoromethylphenyl, 2,6-dichloro-4-fluoromethoxyphenyl, 2,6-dichloro-4-methylphenyl, 2,6-dichloro-4-methoxyphenyl, 2,4,6-trichlorophenyl, 2-chloro-4-trifluoromethoxyphenyl, 2-chloro-4-bromophenyl, 2-chloro-4-difluoromethylphenyl, 2-chloro-4-difluoromethoxyphenyl, 2-chloro-4-fluoromethylphenyl, 2-chloro-4-fluoromethoxyphenyl, 2-chloro-4-methylphenyl, 2-chloro-4-methoxyphenyl, 2,4-dichlorophenyl, and 2-chloro-4-bromophenyl.

8. A compound of the following structure:

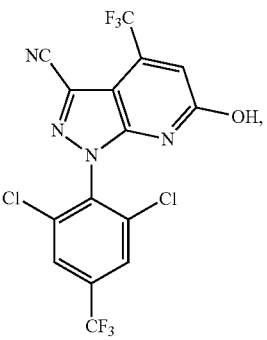 [SMILES: N#Cc1nn(-c2c(Cl)cc(C(F)(F)F)cc2Cl)c2nc(O)cc(C(F)(F)F)c12]

in free or salt form.

9. A compound according to claim 1, wherein the compound is:

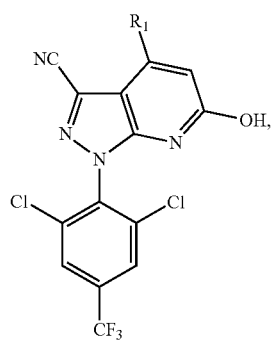

in free or salt form, wherein $R^1$ is selected from H, halo, cyano, nitro, hydroxy, amino, $C_{1-6}$alkyl, $C_{3-6}$cycloalkyl, $C_{1-6}$haloalkyl, $C_{1-6}$alkoxy, $C_{1-6}$haloalkoxy, $C_{3-6}$cycloalkoxy, $C_{3-6}$halocycloalkyl, $NH(C_{1-6}$alkyl), $N(C_{1-6}$alkyl)($C_{1-6}$alkyl), and 3-6 membered heterocycloalkyl.

10. The compound according to claim 9, wherein $R^1$ is selected from halo, cyano, $C_{1-3}$alkyl, $C_{3-6}$cycloalkyl, and $C_{1-3}$haloalkyl (e.g., trifluoromethyl).

11. The compound according to claim 9, wherein the compound is selected from the group consisting of:

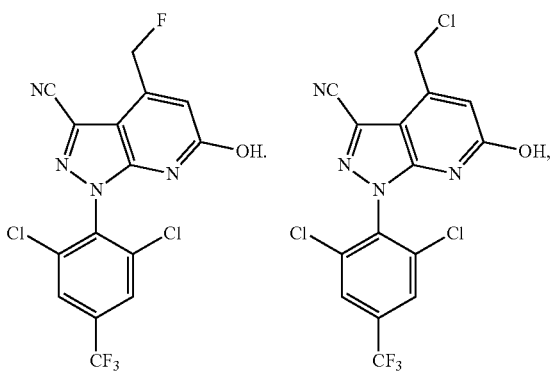

67
-continued

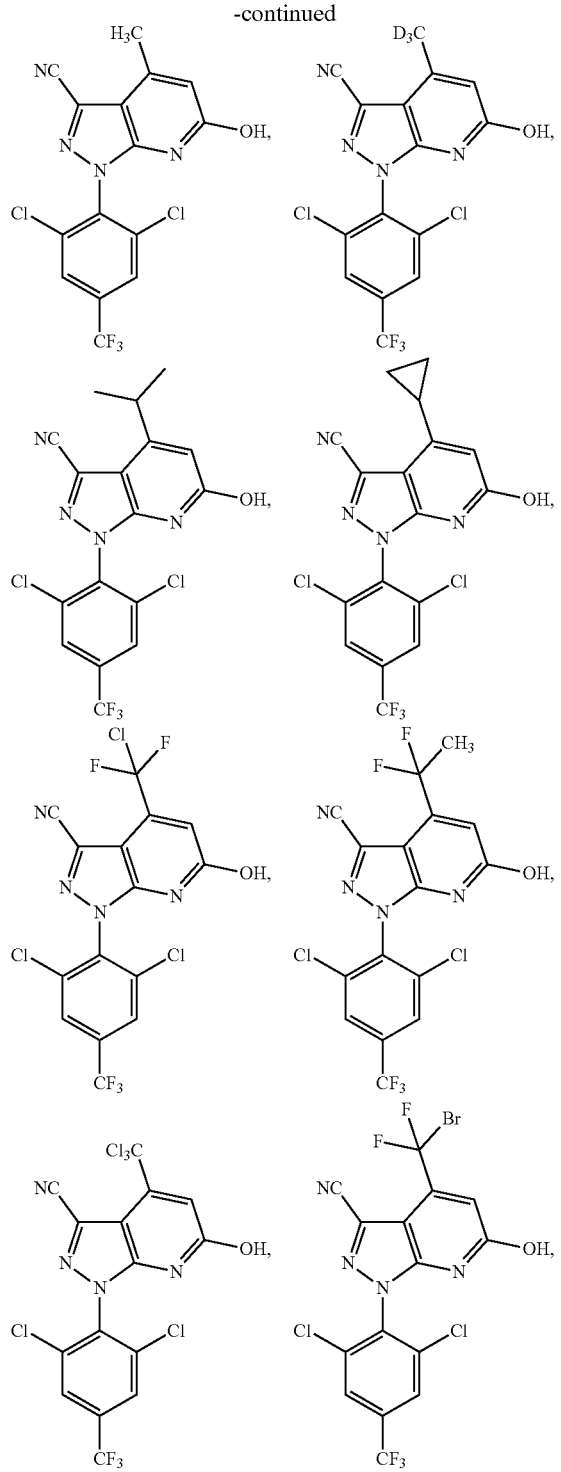

68
-continued

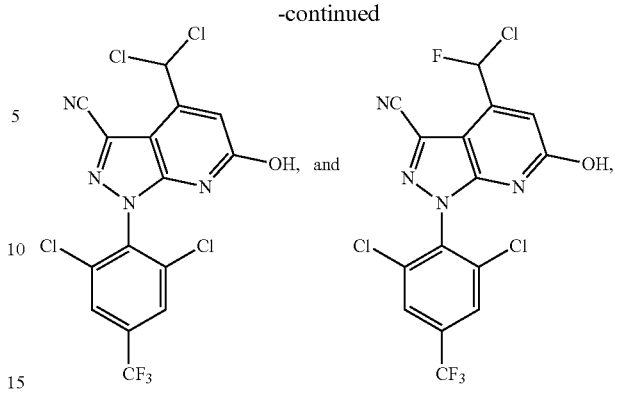

each in free or salt form.

12. A pharmaceutical or insecticidal composition comprising an effective amount of a compound according to claim 1, in free or salt form, in admixture with a pharmaceutically acceptable or insecticidally acceptable diluent or carrier.

13. A pharmaceutical or insecticidal composition comprising an effective amount of a compound according to claim 11, in free or salt form, in admixture with a pharmaceutically acceptable or insecticidally acceptable diluent or carrier, wherein the composition is formulated for delivery by spray.

14. The composition according to claim 13, wherein the composition is a solution comprising the compound dissolved in 2-butoxyethanol, ethanol, and water in a 7:2:1 v/v ratio.

15. A method for the treatment, control, suppression, or eradication, of an infection or infestation of an arthropod, comprising administering or applying an effective amount of a compound according to claim 1.

16. The method according to claim 15, wherein the arthropod is selected from one or more of fleas, ticks, mites, lice, fire ants, termites, beetles, cockroaches, mole crickets, *thrips*, rootworms, and weevils.

17. The method according to claim 15, wherein the arthropod is *Dermanyssus gallinae*.

18. The method according to claim 15, wherein the compound or composition is administered to chickens or applied to chicken coops, chicken pens, chicken cages, other chicken enclosures, chicken farms, or chicken feed.

19. The compound of claim 1, wherein $R^1$ is selected from F, Cl, cyano, methyl, ethyl, and trifluoromethyl, and wherein $R^2$ is selected from H, F, Cl, and cyano, and wherein each R is independently selected from F, Cl, Br, I, cyano, nitro, hydroxy, trifluoromethyl, trifluoromethoxy, and 2,2-difluorocyclopropyl.

20. The compound according to claim 10, wherein $R^1$ is selected from F, Cl, cyano, methyl, ethyl, cyclopropyl, and trifluoromethyl.

* * * * *